United States Patent [19]

Umezawa et al.

[11] 4,410,516

[45] Oct. 18, 1983

[54] 1-N(αHYDROXY-ω-AMINOALKANOYL) DERIVATIVES OF 5,3',4'-TRIDEOXY- OR 5,3', 4'-TRIDEOXY-6'-N- METHYL- OR 5, 3', 4',6''-TETRADEOXYKANNAMYCI B AND PRODUCTION THEREOF

[75] Inventors: Hamao Umezawa, Tokyo; Shinichi Kondo, Yokohama, both of Japan

[73] Assignee: Zaidan Hojin Biseibutsu Kagaku Kenkyu Kai, Tokyo, Japan

[21] Appl. No.: 285,550

[22] Filed: Jul. 21, 1981

[51] Int. Cl.³ .................. A61K 31/71; C07H 15/22
[52] U.S. Cl. .................. 424/180; 536/13.7; 536/13.8
[58] Field of Search .......... 424/180; 536/10, 13.7, 536/13.8

[56] References Cited

U.S. PATENT DOCUMENTS

| | | | |
|---|---|---|---|
| 3,925,353 | 12/1975 | Umezawa et al. | 536/10 |
| 3,929,762 | 12/1975 | Umezawa et al. | 536/10 |
| 3,940,382 | 2/1976 | Umezawa et al. | 536/10 |
| 4,044,123 | 8/1977 | Daniels et al. | 536/10 |
| 4,104,372 | 8/1978 | Umezawa et al. | 536/10 |
| 4,107,424 | 8/1978 | Umezawa et al. | 536/10 |
| 4,147,861 | 4/1979 | Umezawa et al. | 536/10 |

*Primary Examiner*—Johnnie R. Brown
*Attorney, Agent, or Firm*—Larson and Taylor

[57] ABSTRACT

New antibacterial compounds are provided, including a 1-N-(α-hydroxy-ω-aminoalkanoyl)-5,3',4'-trideoxykanamycin B; a 1-N(α-hydroxy-ω-aminoalkanoyl)-5,3',4',641 -tetradeoxykanamycin B; and a 1-N-(α-hydroxy-ω-aminoalkanoyl)-5,3',4'-trideoxy-6'-N-methylkanamycin B; as well as 5,3',4',6''-tetradeoxykanamycin B and 5,3',4'-trideoxy-6'-N-methylkanamycin B.

9 Claims, No Drawings

1-N(αHYDROXY-ω-AMINOALKANOYL) DERIVATIVES OF 5,3',4'-TRIDEOXY- OR 5,3', 4'-TRIDEOXY-6'-N- METHYL- OR 5, 3', 4',6"-TETRADEOXYKANNAMYCI B AND PRODUCTION THEREOF

BACKGROUND OF THE INVENTION

1. Field of the Invention

This invention relates to new semi-synthetic aminoglycosidic antibiotics, including a 1-N-[α-hydroxy-ω-aminoalkanoyl]-5,3',4'-trideoxykanamycin B; 1-N-[α-hydroxy-ω-aminoalkanoyl]-5,3',4',6"-tetradeoxykanamycin B and 5,3',4',6"-tetradeoxykanamycin B as well as a 1-N-[α-hydroxy-ω-aminoalkanoyl]-5,3',4'-trideoxy-6'-N-methylkanamycin B and 5,3',4'-trideoxy-6'-N-methylkanamycin B which are each the new compound useful as antibacterial agent. This invention also relates to processes for the production of these new compounds. This invention further relates to an antibacterial composition comprising one of these new compounds as the active ingredient.

2. Description of the Prior Art

Dibekacin, namely 3',4'-dideoxykanamycin B was semi-synthetically produced from kanamycin B by the present inventors (see Japanese patent publication No. 7595/75; Japanese patent No. 794,612; U.S. Pat. No. 3,753,973). Dibekacin has been used extensively in therapeutic treatment of various bacterial infections as a chemotherapeutic agent which is active against the kanamycin-sensitive bacteria and also against various kanamycin-resistant bacteria. We, the present inventors, produced semi-synthetically habekacin, namely 1-N-(L-4-amino-2-hydroxybutyryl)-dibekacin which is a chemotherapeutic agent effective against dibekacin-resistant bacteria (see Japanese patent publication No. 33,629/77; U.S. Pat. No. 4,107,424). We also produced semi-synthetically a 1-N-[α-hydroxy-ω-aminoalkanoyl]-6'-N-methyldibekacin which has been found to be highly active against various strains of bacteria (Japanese patent application No. 115199/74; U.K. Pat. No. 1,475,481; U.S. Pat. No. 4,147,861). In our further researches, we produced synthetically the 6"-deoxy or 4",6"-dideoxy derivatives of dibekacin and habekacin, i.e., 1-N-(L-4-amino-2-hydroxybutyryl)-dibekacin, respectively. Furthermore, we have found that these 6"-deoxy derivatives and 4",6"-dideoxy derivatives of dibekacin or habekacin exhibit not only a low oto-toxicity but also show an antibacterial activity as high as that of dibekacin or habekacin (see Japanese patent application No. 119323/79; U.K. patent application GB 2 058 774 A and U.S. patent application Ser. No. 174,630), now U.S. Pat. No. 4,332,794.

We also produced 5,3',4'-trideoxykanamycin B as a further deoxy derivative of dibekacin (Japanese Journal of Antibiotics, 32, S-178, (1979)). However, it has been found that 5,3',4'-trideoxykanamycin B is less active than dibekacin.

It may be added that we further have produced some deoxy derivatives of 1-N-(L-4-amino-2-hydroxybutyryl)kanamycin A (ie. amikacin), including 3'-deoxyamikacin (Japanese patent application No. 49105/75; U.S. Pat. No. 4,104,372), 3',4'-dideoxyamikacin (Japanese patent application No. 11402/79; U.K. patent application No. GB 2043 034 A, U.S. patent application Ser. No. 114,779 now U.S Pat. No. 4,298,727); 6"-deoxyamikacin (Japanese patent application No. 54733/79); 4",6"-dideoxyamikacin (Japanese patent application No. 54733/79); 3',4',4",6"-tetradeoxyamikacin (Japanese patent application No. 138685/79) and 3',4',6"-trideoxyamikacin (Japanese patent application No. 5657/80), as well as 3',6"-dideoxyamikacin; 5,3'-dideoxyamikacin and 5,3',6"-trideoxyamikacin (Japanese patent application No. 107202/80) which all have a low acute toxicity and a low oto-toxicity with exhibiting a useful antibacterial activity as high as that of amikacin.

SUMMARY OF THE INVENTION

In further development of our researches on the deoxy derivatives of dibekacin or habekacin, we have now succeeded to produce a new compound, 5,3',4',6"-tetradeoxykanamycin B which has been found to be significantly active against some kinds of bacteria, though the 5,3',4'-trideoxykanamycin B exhibits no useful anti-bacterial activity. We have also succeeded to produce a new compound, 5,3',4'-trideoxy-6'-N-methylkanamycin B which also exhibits an antibacterial activity higher than that of the 5,3',4'-trideoxykanamycin B especially against some resistant strains. In an attempt to produce such new derivatives of 5,3',4'-trideoxykanamycin B, 5,3',4',6"-tetradeoxykanamycin B or 5,3',4'-trideoxy-6'-N-methylkanamycin B which will have improved antibacterial activity, we have now synthetized new 1-N-[α-hydroxy-ω-aminoalkanoyl] derivatives of these deoxykanamycins B by acylating the 1-amino group of the deoxykanamycin B with an α-hydroxy-ω-aminoalkanoic acid. Then, we have discovered that the resultant new 1-N-[α-hydroxy-ω-aminoalkanoyl] derivatives of 5,3',4'-trideoxykanamycin B, 5,3',4'-trideoxy-6'-N-methylkanamycin B, and 5,3',4',6"-tetradeoxykanamycin B are very much active against kanamycin-sensitive and kanamycin-resistant bacteria and also exhibit a high antibacterial activity against a wide range of bacteria.

According to the first, most generic aspect of this invention, therefore, there is provided as the new compound a 1-N-[α-hydroxy-ω-aminoalkanoyl]-5,3',4'-trideoxy- or 1-N-[α-hydroxy-ω-aminoalkanoyl]-5,3',4'-trideoxy-6'-N-methylkanamycin B or 5,3',4'-trideoxy-6'-N-methylkanamycin B or a 1-N-[α-hydroxy-ω-aminoalkanoyl]-5,3',4',6"-tetradeoxykanamycin B or 5,3',4',6"-tetradeoxykanamycin B represented by the formula (I)

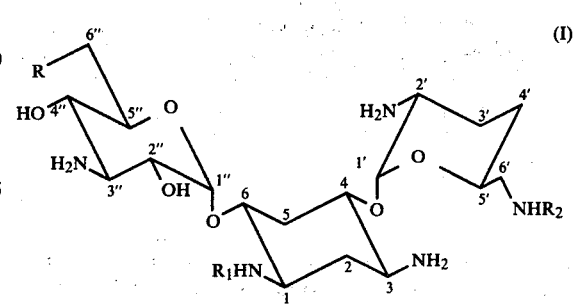

wherein R is a hydroxyl group or a hydrogen atom, $R_1$ is a hydrogen atom or an α-hydroxy-ω-aminoalkanoyl group of formula

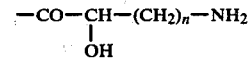

where n is an integer of 1, 2 or 3, and $R_2$ is a hydrogen atom or a methyl group, provided that $R_2$ is not the methyl group when R is the hydrogen atom, or a pharmaceutically acceptable acid-addition salt of said compound.

According to the first preferred embodiment of the first aspect invention, there is provided a new compound which belongs to the new compound of the above formula (I) and is a 1-N-[α-hydroxy-ω-aminoalkanoyl]-5,3',4'-trideoxykanamycin B or 1-N-[α-hydroxy-ω-aminoalkanoyl]-5,3',4',6"-tetradeoxykanamycin B represented by the formula (II)

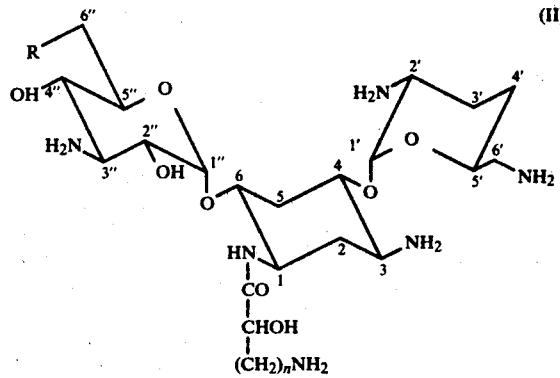

(II)

wherein R is a hydroxyl group or a hydrogen atom and n is an integer of 1, 2 or 3 and wherein R is the hydroxyl group when the compound of the formula (II) is a 1-N-[α-hydroxyl-ω-aminoalkanoyl]-5,3',4'-trideoxykanamycin B but R is the hydrogen atom when the compound of the formula (II) is a 1-N-[α-hydroxy-ω-aminoalkanoyl]-5,3',4',6"-tetradeoxykanamycin B, or a pharmaceutically acceptable acid-addition salt of the compound (II).

According to the second preferred embodiment of the first aspect invention, there is provide a new compound which belongs to the compound of the formula (I) and is 5,3',4',6"-tetradeoxykanamycin B represented by the formula (III)

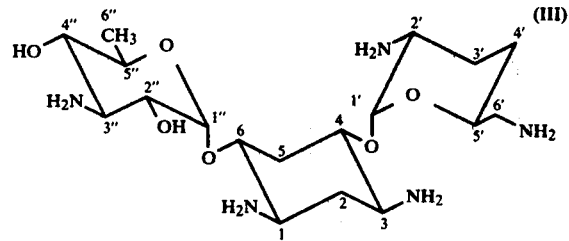

(III)

or a pharmaceutically acceptable acid-addition salt of the compound (III).

The physico-chemical and biological properties of the new compounds of the formulae (II) and (III) according to the first and second preferred embodiments of the first aspect invention are as follows:

(1) 1-N-[(S)-4-amino-2-hydroxybutyryl]-5,3',4'-trideoxykanamycin B monocarbonate monohydrate is a substance in the form of a colorless powder decomposing at 163°–166° C. and showing a specific optical rotation $[α]_D^{26} = +87°$ (c 1, water). Its elemental analysis is coincident with the theoretical values of $C_{22}H_{44}N_6O_9 \cdot H_2CO_3 \cdot H_2O$ (C 44.80%, H 7.85%, N 13.63%). This substance gives a single spot (positive to ninhydrin) at Rf 0.05 and at Rf 0.09 in a thin layer chromatography on silica gel developed with butanol-ethanol-chloroform-17% aqueous ammonia (4:5:2:5 by volume) and with chloroform-methanol-conc. aqueous ammonia-water (1:4:2:1 by volume) as the development solvent, respectively.

(2) 1-N-[(RS)-3-amino-2-hydroxypropionyl]-5,3',4'-trideoxykanamycin B monocarbonate is a substance in the form of a colorless powder decomposing at 113°–116° C. and showing a specific optical rotation $[α]_D^{27} = +120°$ (c 1, water). Its elemental analysis is coincident with the theoretical values of $C_{21}H_{42}N_6O_9 \cdot H_2CO_3$ (C 42.85%, H 7.19%, N 13.63%). This substance gives a single spot (positive to ninhydrin) at Rf 0.12 and at Rf 0.35 in the abovementioned thin layer chromatography on silica gel developed with butanol-ethanol-chloroform-17% aqueous ammonia (4:5:2:5 by volume) and with chloroform-methanol-conc. aqueous ammonia-water (1:4:2:1 by volume) as the development solvent, respectively.

(3) 1-N-[(S)-4-amino-2-hydroxybutyryl]-5,3',4',6"-tetradeoxykanamycin B dicarbonate is a substance in the form of a colorless powder decomposing at 131°–135° C. and showing a specific optical rotation $[α]_D^{27} = +90°$ (c 1, water). Its elemental analysis is coincident with the theoretical values of $C_{22}H_{44}N_6O_8 \cdot 2H_2CO_3$ (C 44.71%, H 7.50%, N 13.04%). This substance gives a single spot (positive to ninhydrin) at Rf 0.07 and at Rf 0.23 in the above-mentioned thin layer chromatography on silica gel developed with butanol-ethanol-chloroform-17% aqueous ammonia (4:5:2:5 by volume) and with chloroform-methanol-conc. aqueous ammonia-water (1:4:2:1 by volume) as the development solvent, respectively.

(4) 5,3',4',6"-tetradeoxykanamycin B dicarbonate monohydrate is a substance in the form of a colorless powder decomposing at 128°–136° C. and showing a specific optical rotation $[α]_D^{23} = +102°$ (c 1, water). Its elemental analysis is coincident with the theoretical values of $C_{18}H_{37}N_5O_6 \cdot 2H_2CO_3 \cdot H_2O$ (C 42.77%, H 7.72%, N 12.47%). This substance gives a single spot (positive to ninhydrin) at Rf 0.42 and at Rf 0.56 in the above-mentioned thin layer chromatography on silica gel developed with butanol-ethanol-chloroform-17% aqueous ammonia (4:5:2:5 by volume) and with chloroform-methanol-conc. aqueous ammonia-water (1:4:2:1 by volume) as the development solvent, respectively.

The minimum inhibitory concentration (mcg/ml) of 1-N-[(S)-4-amino-2-hydroxybutyryl]-5,3',4'-trideoxykanamycin B (abbreviated as AHB-trideoxyKMB), 1-N-[(RS)-3-amino-2-hydroxypropionyl]-5,3',4'-trideoxykanamycin B (abbreviated as AHP-trideoxyKMB) and 1-N-[(S)-4-amino-2-hydroxybutyryl]-5,3',4',6"-tetradeoxykanamycin B (abbreviated as AHB-tetradeoxyKMB) of the formula (II) according to this invention as well as of the new compound 5,3',4',6"-tetradeoxykanamycin B (abbreviated as tetradeoxyKMB) of the formula (III) according to this invention against various microorganisms were determined according to serial dilution method on a nutrient agar medium at 37° C., the estimation being made after 18 hours incubation. For comparison purpose, the minimum inhibitory concentrations of habekacin were also determined in the same manner as stated above.

The antibacterial spectra of these new and known substances are shown in Table 1 below.

TABLE 1

| Test organisms | MIC. (mcg/ml) | | | | |
|---|---|---|---|---|---|
| | AHB-tri-deoxyKMB | AHP-tri-deoxyKMB | AHB-tetra-deoxyKMB | Habekacin (Comparative) | Tetradeoxy-KMB |
| Staphylococcus aureus 209P | <0.20 | <0.20 | <0.20 | 0.39 | 3.13 |
| Staphylococcus aureus Smith | <0.20 | <0.20 | <0.20 | <0.20 | <0.20 |
| Staphylococcus aureus AP01 | 0.39 | 0.78 | 0.78 | 0.78 | 6.25 |
| Staphylococcus epidermidis 109 | 0.39 | 0.78 | 0.78 | 0.78 | 6.25 |
| Micrococcus flavus FDA 16 | 1.56 | 6.25 | 6.25 | 1.56 | 50 |
| Sarcina lutea PCI 1001 | 0.39 | 0.78 | 0.78 | 1.56 | 50 |
| Bacillus anthracis | <0.20 | <0.20 | <0.20 | <0.20 | 0.39 |
| Bacillus subtilis PCI 219 | <0.20 | <0.20 | <0.20 | <0.20 | <0.20 |
| Bacillus subtilis NRRL B-558 | <0.20 | <0.20 | <0.20 | <0.20 | <0.20 |
| Bacillus cereus ATCC 10702 | 0.78 | 0.78 | 0.39 | 1.56 | 3.13 |
| Mycobacterium smegmatis ATCC 607 | 0.20 | 0.20 | <0.20 | 0.39 | 0.78 |
| Escherichia coli NIHJ | 0.78 | 1.56 | 0.78 | 3.13 | 6.25 |
| Escherichia coli K-12 | 0.78 | 1.56 | 0.78 | 3.13 | 25 |
| Escherichia coli K-12 R5 | 100 | 100 | 50 | 100 | >100 |
| Escherichia coli K-12 R 388 | 0.78 | 1.56 | 0.39 | 1.56 | 3.13 |
| Escherichia coli K-12 J5R 11-2 | 0.78 | 1.56 | 0.78 | 1.56 | 6.25 |
| Escherichia coli K-12 ML 1629 | 1.56 | 3.13 | 0.78 | 3.13 | 6.25 |
| Escherichia coli K-12 ML 1630 | 1.56 | 3.13 | 1.56 | 3.13 | 12.5 |
| Escherichia coli K-12 ML 1410 | 1.56 | 1.56 | 1.56 | 6.25 | 12.5 |
| Escherichia coli K-12 ML 1410 R81 | 1.56 | 1.56 | 0.78 | 3.13 | 6.25 |
| Escherichia coli K-12 LA 290 R55 | 3.13 | 3.13 | 1.56 | 6.25 | >100 |
| Escherichia coli K-12 LA 290 R56 | 0.78 | 1.56 | 0.39 | 3.13 | 100 |
| Escherichia coli K-12 LA 290 R64 | 0.78 | 1.56 | 0.78 | 3.13 | 100 |
| Escherichia coli W677 | 0.78 | 1.56 | 0.78 | 3.13 | 6.25 |
| Escherichia coli JR66/W677 | 1.56 | 3.13 | 1.56 | 6.25 | >100 |
| Escherichia coli K-12 C 600R/35 | 0.78 | 1.56 | 0.78 | 1.56 | 6.25 |
| Escherichia coli JR255 | 0.39 | 1.56 | 0.78 | 3.13 | 25 |
| Klebsiella pneumoniae PCI 602 | 0.78 | 1.56 | 0.78 | 1.56 | 3.13 |
| Klebsiella pneumoniae 22 #3038 | 3.13 | 6.25 | 1.56 | 3.13 | 100 |
| Shigella dysenteriae JS 11910 | 3.13 | 6.25 | 1.56 | 12.5 | 12.5 |
| Shigella flexneri 4b JS11811 | 3.13 | 6.25 | 1.56 | 6.25 | 25 |
| Shigella sonnei JS11746 | 3.13 | 6.25 | 3.13 | 6.25 | 12.5 |
| Salmonella typhi T-63 | 25 | 50 | 25 | 1.56 | 12.5 |
| Salmonella enteritidis 1891 | 3.13 | 6.25 | 3.13 | 3.13 | 25 |
| Proteus vulgaris OX19 | 0.39 | 0.78 | 0.39 | 0.78 | 1.56 |
| Proteus rettgeri GN311 | 25 | 25 | 25 | 50 | >100 |
| Proteus rettgeri GN466 | 3.13 | 3.13 | 1.56 | 12.5 | 25 |
| Serratia marcescens | 25 | 25 | 25 | 50 | 100 |
| Serratia SOU | 100 | >100 | 100 | >100 | >100 |
| Serratia 4 | 12.5 | 25 | 25 | 50 | 50 |
| Providencia Pv 16 | 12.5 | 25 | 25 | 25 | >100 |
| Providencia 2991 | 6.25 | 25 | 25 | 50 | >100 |
| Pseudomonas aeruginosa A3 | 0.39 | 0.78 | 0.78 | 3.13 | 3.13 |
| Pseudomonas aeruginosa No. 12 | 3.13 | 3.13 | 6.25 | 3.13 | 25 |
| Pseudomonas aeruginosa H9 | 3.13 | 3.13 | 3.13 | 6.25 | 100 |
| Pseudomonas aeruginosa H11 | 6.25 | 6.25 | 12.5 | 12.5 | 25 |
| Pseudomonas aeruginosa TI-13 | 3.13 | 3.13 | 3.13 | 3.13 | 12.5 |
| Pseudomonas aeruginosa GN315 | 25 | 50 | 100 | 6.25 | >100 |
| Pseudomonas aeruginosa 99 | 3.13 | 3.13 | 6.25 | 6.25 | 25 |
| Pseudomonas aeruginosa B-13 | 6.25 | 12.5 | 12.5 | 25 | 50 |
| Pseudomonas aeruginosa 21-75 | 6.25 | 12.5 | 12.5 | 25 | >100 |
| Pseudomonas aeruginosa PST1 | 6.25 | 6.25 | 6.25 | 25 | >100 |
| Pseudomonas aeruginosa ROS134/PU21 | >100 | >100 | 100 | >100 | >100 |
| Pseudomonas aeruginosa K-Ps102 | 1.56 | 3.13 | 3.13 | 3.13 | 12.5 |
| Pseudomonas maltophilia GN907 | >100 | >100 | >100 | >100 | >100 |

According to the third preferred embodiment of the first aspect invention, there is provided a new compound which belongs to the compound of the formula (I) and is a 1-N-[α-hydroxy-ω-aminoalkanoyl]-5,3',4'-trideoxy-6'-N-methylkanamycin B represented by the formula (IV)

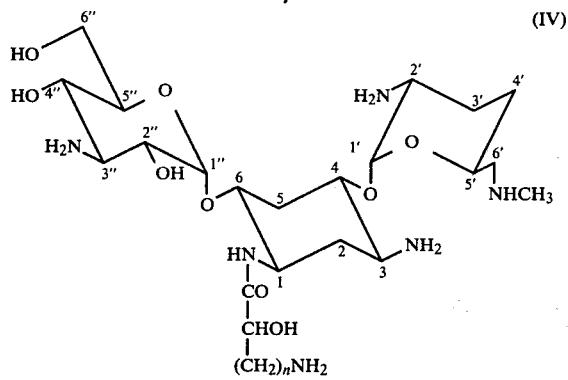

(IV)

wherein n is an integer of 1, 2 or 3, or a pharmaceutically acceptable acid-addition salt of the compound (IV).

According to the fourth preferred embodiment of the first aspect invention, there is further provided a new compound which belongs to the compound of the formula (I) and is 5,3′,4′-trideoxy-6′-N-methylkanamycin B represented by the formula (V)

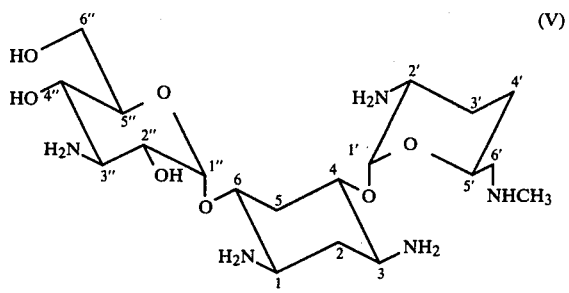

(V)

or a pharmaceutically acceptable acid-addition salt of the compound (V).

The physico-chemical and biological properties of the new compounds of the formulae (IV) and (V) according to the third and fourth preferred embodiment of the first aspect invention are as follows:

(5) 1-N-[(S)-4-amino-2-hydroxybutyryl]-5,3′,4′-trideoxy-6′-N-methylkanamycin B monocarbonate is a substance in the form of a colorless powder decomposing at 162°–165° C. and showing a specific optical rotation $[\alpha]_D^{22} = +88°$ (c 1, water). Its elemental analysis is coincident with the theoretical values of $C_{23}H_{46}N_6O_9 \cdot H_2CO_3$ (C 47.05%, H 7.90%, N 13.72%). This substance gives a single spot (positive to ninhydrin) at Rf 0.05 and at Rf 0.08 in a thin layer chromatography on silica gel developed with butanol-ethanol-chloroform-17% aqueous ammonia (4:5:2:5 by volume) and with chloroform-methanol-conc. aqueous ammonia-water (1:4:2:1 by volume) as the development solvent, respectively.

(6) 1-N-[(RS)-3-amino-2-hydroxypropionyl]-5,3′,4′-trideoxy-6′-N-methylkanamycin B monocarbonate monohydrate is a substance in the form of a colorless powder decomposing at 162°–164° C. and showing a specific option rotation $[\alpha]_D^{23} = +80°$ (c 0.5, water). Its elemental analysis is coincident with the theoretical values of $C_{22}H_{44}N_6O_9 \cdot H_2CO_3 \cdot H_2O$ (C 44.80%, H 7.85%, N 13.62%). This substance gives a single spot (positive to ninhydrin) at Rf 0.05 and at Rf 0.14 in the above-mentioned thin layer chromatography on silica gel developed with butanol-ethanol-chloroform-17% aqueous ammonia (4:5:2:5 by volume) and with chloroform-methanol-conc. aqueous ammonia-water (1:4:2:1 by volume) as the development solvent, respectively.

(7) 1-N-[(S)-5-amino-2-hydroxyvaleryl]-5,3′,4′-trideoxy-6′-N-methylkanamycin B monocarbonate monohydrate is a substance in the form of a colorless powder decomposing at 163°–166° C. and showing a specific optical rotation $[\alpha]_D^{23} = +84°$ (c 0.5, water). Its elemental analysis is coincident with the theoretical values of $C_{24}H_{48}N_6O_9 \cdot H_2CO_3 \cdot H_2O$ (C 46.57%, H 8.13%, N 13.03%). This substance gives a single spot (positive to ninhydrin) at Rf 0.03 and at Rf 0.08 in the above-mentioned thin layer chromatography on silica gel developed with butanol-ethanol-chloroform-17% aqueous ammonia (4:5:2:5 by volume) and with chloroform-methanol-conc. aqueous ammonia-water (1:4:2:1 by volume) as the development solvent, respectively.

(8) 5,3′,4′-Trideoxy-6′-N-methylkanamycin B monocarbonate monohydrate is a substance in the form of a colorless powder decomposing at 137°–140° C. and showing a specific optical rotation $[\alpha]_D^{22} = +66°$ (c 1, water). Its elemental analysis is coincident with the theoretical values of $C_{19}H_{39}N_5O_7 \cdot H_2CO_3 \cdot H_2O$ (C 45.36%, H 8.18%, N 13.23%). This substance gives a single spot (positive to ninhydrin) at Rf 0.22 and at Rf 0.49 in the above-mentioned thin layer chromatography on silica gel developed with butanol-ethanol-chloroform-17% aqueous ammonia (4:5:2:5 by volume) and with chloroform-methanol-conc. aqueous ammonia-water (1:4:2:1 by volume) as the development solvent, respectively.

The minimum inhibitory concentrations (mcg/ml) of 1-N-[(S)-4-amino-2-hydroxybutyryl]-5,3′,4′-trideoxy-6′-N-methylkanamycin B (abbreviated as AHB-trideoxyMKMB), 1-N-[(RS)-3-amino-2-hydroxypropionyl]-5,3′,4′-trideoxy-6′-N-methylkanamycin B (abbreviated as AHP-trideoxyMKMB) and 1-N-[(S)-5-amino-2-hydroxyvaleryl]-5,3′,4′-trideoxy-6′-N-methylkanamycin B (abbreviated as AHV-trideoxyMKMB) of the formula (IV) according to this invention as well as of the new compound 5,3′,4′-trideoxy-6′-N-methylkanamycin B (abbreviated as trideoxyMKMB) of the formula (V) according to this invention against various microorganisms were determined according to serial dilution method on a nutrient agar medium at 37° C., the estimation being made after 18 hours incubation. For comparison purpose, the minimum inhibitory concentrations of 1-N-[(S)-4-amino-2-hydroxybutyryl]-3′,4′-dideoxykanamycin B (ie. habekacin) were also determined in the same manner as stated above.

The antibacterial spectra of these new and known compounds are shown in Table 2 below.

TABLE 2

| | MIC. (mcg/ml) | | | | |
|---|---|---|---|---|---|
| Test organisms | AHB-trideoxyMKMB | AHP-trideoxyMKMB | AHV-trideoxyMKMB | Habekacin (Comparative) | Trideoxy-MKMB |
| *Staphylococcus aureus* 209P | <0.20 | 0.39 | 0.20 | 0.39 | 1.56 |
| *Staphylococcus aureus* Smith | <0.20 | <0.20 | <0.20 | <0.20 | 0.39 |
| *Staphylococcus aureus* AP01 | 0.39 | <0.20 | 0.39 | 0.78 | 25 |

TABLE 2-continued

| Test organisms | MIC. (mcg/ml) | | | | |
|---|---|---|---|---|---|
| | AHB-tri-deoxyMKMB | AHP-tri-deoxyMKMB | AHV-tri-deoxyMKMB | Habekacin (Comparative) | Trideoxy-MKMB |
| *Staphylococcus epidermidis* 109 | <0.20 | <0.20 | <0.20 | 0.78 | 6.25 |
| *Micrococcus flavus* FDA 16 | 1.56 | 3.13 | 3.13 | 1.56 | 100 |
| *Sarcina lutea* PCI 1001 | 0.39 | 0.78 | 1.56 | 1.56 | 25 |
| *Bacillus anthracis* | <0.20 | <0.20 | <0.20 | <0.20 | 0.78 |
| *Bacillus subtilis* PCI 219 | <0.20 | 0.39 | <0.20 | <0.20 | <0.20 |
| *Bacillus subtilis* NRRL B-558 | <0.20 | 0.39 | <0.20 | <0.20 | 0.78 |
| *Bacillus cereus* ATCC 10702 | 0.39 | 1.56 | 1.56 | 1.56 | 12.5 |
| *Mycobacterium smegmatis* ATCC 607 | <0.20 | 0.39 | 0.39 | 0.39 | 6.25 |
| *Escherichia coli* NIHJ | 0.78 | 3.13 | 1.56 | 3.13 | 12.5 |
| *Escherichia coli* K-12 | 0.78 | 3.13 | 1.56 | 3.13 | 12.5 |
| *Escherichia coli* K-12 R5 | 3.13 | 12.5 | 6.25 | 100 | 50 |
| *Escherichia coli* K-12 R 388 | 0.39 | 1.56 | 1.56 | 1.56 | 12.5 |
| *Escherichia coli* K-12 J5R 11-2 | 1.56 | 3.13 | 3.13 | 1.56 | 25 |
| *Escherichia coli* K-12 ML 1629 | 0.78 | 3.13 | 3.13 | 3.13 | 25 |
| *Escherichia coli* K-12 ML 1630 | 1.56 | 3.13 | 3.13 | 3.13 | 25 |
| *Escherichia coli* K-12 ML 1410 | 1.56 | 3.13 | 3.13 | 6.25 | 25 |
| *Escherichia coli* K-12 ML 1410 R81 | 1.56 | 3.13 | 3.13 | 3.13 | 25 |
| *Escherichia coli* K-12 LA 290 R55 | 1.56 | 6.25 | 3.13 | 6.25 | 100 |
| *Escherichia coli* K-12 LA 290 R56 | 0.78 | 3.13 | 1.56 | 3.13 | 25 |
| *Escherichia coli* K-12 LA 290 R64 | 1.56 | 3.13 | 1.56 | 3.13 | 25 |
| *Escherichia coli* W677 | 1.56 | 3.13 | 1.56 | 3.13 | 12.5 |
| *Escherichia coli* JR66/W677 | 1.56 | 6.25 | 3.13 | 6.25 | 100 |
| *Escherichia coli* K-12 C 600R/35 | 1.56 | 1.56 | 1.56 | 1.56 | 12.5 |
| *Escherichia coli* JR255 | 0.78 | 3.13 | 1.56 | 3.13 | 100 |
| *Klebsiella pneumoniae* PCI 602 | 0.78 | 3.13 | 1.56 | 1.56 | 12.5 |
| *Klebsiella pneumoniae* 22 #3038 | 1.56 | 3.13 | 3.13 | 3.13 | 100 |
| *Shigella dysenteriae* JS 11910 | 1.56 | 6.25 | 6.25 | 12.5 | 50 |
| *Shigella flexneri* 4b JS11811 | 0.78 | 3.13 | 1.56 | 6.25 | 25 |
| *Shigella sonnei* JS11746 | 3.13 | 6.25 | 6.25 | 6.25 | 25 |
| *Salmonella typhi* T-63 | 1.56 | 3.13 | 3.13 | 1.56 | 6.25 |
| *Salmonella enteritidis* 1891 | 0.78 | 6.25 | 3.13 | 3.13 | 25 |
| *Proteus vulgaris* OX19 | <0.20 | 0.78 | 0.78 | 0.78 | 3.13 |
| *Proteus rettgeri* GN311 | 50 | 25 | 100 | 50 | 100 |
| *Proteus rettgeri* GN466 | 6.25 | 12.5 | 6.25 | 12.5 | 25 |
| *Serratia marcescens* | 6.25 | 12.5 | 12.5 | 50 | 100 |
| Serratia SOU | 25 | 50 | 50 | >100 | >100 |
| Serratis 4 | 6.25 | 12.5 | 12.5 | 50 | 50 |
| Providencia Pv 16 | 6.25 | 50 | 25 | 25 | >100 |
| Providencia 2991 | 12.5 | 50 | 25 | 50 | >100 |
| *Pseudomonas aeruginosa* A3 | 0.69 | 0.78 | 0.39 | 3.13 | 3.13 |
| *Psuedomonas aeruginosa* No. 12 | 1.56 | 3.13 | 3.13 | 3.13 | 25 |
| *Pseudomonas aeruginosa* H9 | 1.56 | 3.13 | 3.13 | 6.25 | 25 |
| *Pseudomonas aeruginosa* H11 | 12.5 | 12.5 | 6.25 | 12.5 | 25 |
| *Pseudomonas aeruginosa* TI-13 | 1.56 | 3.13 | 1.56 | 3.13 | 12.5 |
| *Pseudomonas aeruginosa* GN315 | 3.13 | 3.13 | 3.13 | 6.25 | 25 |
| *Pseudomonas aeruginosa* 99 | 3.13 | 12.5 | 6.25 | 6.25 | 50 |
| *Pseudomonas aeruginosa* B-13 | 12.5 | 25 | 12.5 | 25 | 100 |
| *Pseudomonas aeruginosa* 21-75 | 12.5 | 25 | 12.5 | 25 | >100 |
| *Pseudomonas aeruginosa* PST1 | 12.5 | 25 | 12.5 | 25 | >100 |
| *Pseudomonas aeruginosa* ROS134/PU21 | 50 | 50 | 50 | >100 | >100 |
| *Pseudomonas aeruginosa* K-Ps102 | 1.56 | 3.13 | 1.56 | 3.13 | 25 |
| *Pseudomonas maltophilia* GN907 | >100 | >100 | >100 | >100 | >100 |

From Tables 1 and 2, it is seen that the new compounds of this invention according to the formula (I), including the compounds of the formulae (II), (III), (IV) and (V), effectively inhibit the growth of many kinds of bacterial strains. The new compounds of this invention show a low acute toxicity to animals, including men. It has been found that the new compounds of the formulae (II) and (III) according to this invention, such as 1-N-[(S)-4-amino-2-hydroxybutyryl]-5,3',4'-trideoxykanamycin B; 1-N-[3-amino-2-hydroxypropionyl]-5,3',4'-trideoxykanamycin B; 1-N-[(S)-4-amino-2-hydroxybutyryl]-5,3',4',6"-tetradeoxykanamycin B; and 5,3',4',6"-tetradeoxykanamycin B exhibit an $LD_{50}$ value of 25 to 50 mg/kg when their acute toxicity is estimated by intravenous injection in mice. It has also been found that the new compounds of the formulae (III) and (IV) according to this invention, such as 1-N-[(S)-4-amino-2-hydroxybutyryl]-5,3',4'-trideoxy-6'-N-methylkanamycin B; 1-N-(3-amino-2-hydroxypropionyl)-5,3',4'-trideoxy-6'-N-methylkanamycin B; 1-N-[(S)-5-amino-2-hydroxyvaleryl]-5,3',4'-trideoxy-6'-N-methylkanamycin B and 5,3',4'-trideoxy-6'-N-methylkanamycin B exhibit an $LD_{50}$ value of 50 to 100 mg/kg when their acute toxicity is estimated by intravenous injection in mice.

The new compounds of this invention are usually obtained in the form of its free base or a hydrate or a carbonate thereof. The new compounds of this invention each may readily be converted into a form of a pharmaceutically acceptable acid addition salt thereof, such as the hydrochloride, hydrobromide, sulfate, phosphate, nitrate, acetate, maleate, citrate, ascorbate, methanesulfonate and the like by reacting with the appropriate, pharmaceutically acceptable inorganic or organic acid in an aqueous medium.

The new compounds of the formula (I), (II), (III), (IV) or (V) according to this invention and its pharmaceutically acceptable acid addition salt may be administered orally, intraperitoneally, intravenously, subcutaneously or intramuscularly using any pharmaceutical form known to the art for such administration and in a similar manner to the known kanamycins. For instance, the new compounds of this invention may be administered orally using any pharmaceutical form known to the art for oral administration. Examples of the pharmaceutical forms for oral administration are powders, capsules, tablets, syrup and the like. A suitable dose of the new compounds of this invention for effective treatment of bacterial infections is in a range of 0.1 to 1 g. per person a day when it is given orally. It is preferred that said dose should be orally administered in three to four aliquots per day. The new compounds of this invention may also be administered by intramuscular injection at a dosage of 50 to 500 mg per person two to four times per day. Moreover, the new compounds of this invention may be formulated into an ointment for external application which contains the active compound at a concentration of 0.5–5% by weight in mixture with a known ointment base such as polyethylene glycol. Furthermore, the new compounds of this invention are each useful for sterilization of surgical instruments and sanitary materials.

According to a second aspect of this invention, therefore, there is provided an antibacterial composition comprising as the active ingredient a 1-N-[α-hydroxy-ω-aminoalkanoyl]-5,3',4'-trideoxykanamycin B, a 1-N-[α-hydroxy-ω-aminoalkanoyl]-5,3',4',6''-tetradeoxykanamycin B or a pharmaceutically acceptable acid-addition salt thereof as defined by the formula (II) or 5,3',4',6''-tetradeoxykanamycin B or a pharmaceutically acceptable acid-addition salt thereof as defined by the formula (III) in an antibacterially effective amount to inhibit the growth of bacteria, in combination with a carrier for the active ingredient compound, as well as an antibacterial composition comprising as the active ingredient a 1-N-[α-hydroxy-ω-aminoalkandyl]-5,3',4'-trideoxy-6'-N-methylkanamycin B or a pharmaceutically acceptable acid addition salt thereof as defined by the formula (IV) or 5,3',4'-trideoxy-6'-N-methylkanamycin B or a pharmaceutically acceptable acid-addition salt thereof as defined by the formula (V), in an antibacterially effective amount to inhibit the growth of bacteria, in combination with a carrier for the active ingredient compound.

Next, the production of the new compound of the formula (II), according to this invention is described. Thus, the new compound of the formula (II) such as 1-N-[(S)-4-amino-2-hydroxybutyryl]-5,3',4'-trideoxykanamycin B and 1-N-[(S)-4-amino-2-hydroxybutyryl]-5,3',4',6''-tetradeoxykanamycin B can be synthetized by using as the starting compound either the known substance 5,3',4'-trideoxykanamycin B (Japanese Journal of Antibiotics, 32, S-178 (1979)) or the new compound 5,3',4',6''-tetradeoxykanamycin B as obtained according to this invention and condensing the 1-amino group of the starting compound with a corresponding α-hydroxy-ω-amino alkanoic acid or a functional equivalent thereof.

According to the third aspect of this invention, therefore, there is provided a process for the production of a 1-N-[α-hydroxy-ω-aminoalkanoyl]-5,3',4'-trideoxykanamycin B or 1-N-[α-hydroxy-ω-aminoalkanoyl]-5,3',4',6''-tetradeoxykanamycin B represented by the formula (II)

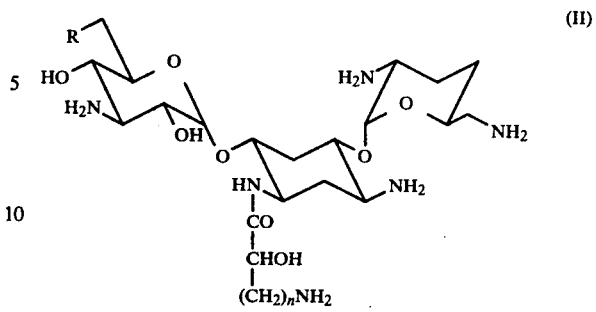

wherein R is a hydroxyl group or a hydrogen atom and n is an integer of 1, 2 or 3, which comprises:

(a) acylating the 1-amino group of 5,3',4'-trideoxykanamycin B or 5,3',4',6''-tetradeoxykanamycin B represented by the formula (VI)

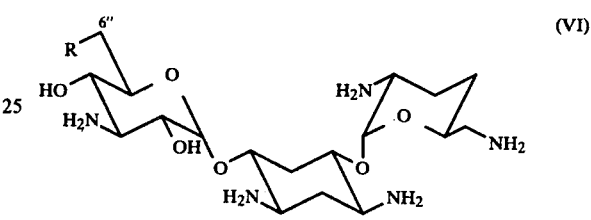

wherein R is as defined above, or a partially amino-protected derivative of 5,3',4'-trideoxykanamycin B or 5,3',4',6''-tetradeoxykanamycin B represented by the formula (VI')

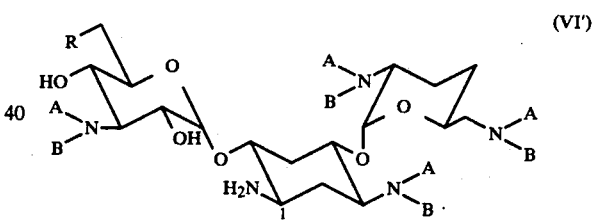

wherein R is a hydroxyl group or a hydrogen atom, and A is a hydrogen atom and at least one B is a mono-valent amino-protecting group but the other B(s) is or are each a hydrogen atom, or at least one pair of A and B taken together form a di-valent amino-protecting group but the other A and B are each a hydrogen atom, and the amino-protecting groups represented by A and B may be equal to each other or different from each other, by reaction with an α-hydroxy-ω-aminoalkanoic acid or an amino-protected derivative thereof represented by the formula (VII)

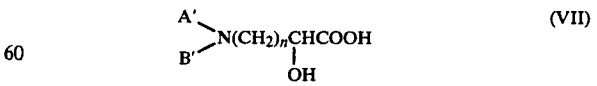

wherein A' is a hydrogen atom and B' is a hydrogen atom or a mono-valent amino-protecting group, or A' and B' taken together form a di-valent amino-protecting group and n is an integer of 1, 2 or 3, or a functional equivalent of the compound (VII), to produce the 1-N-acylated product represented by the formula (II')

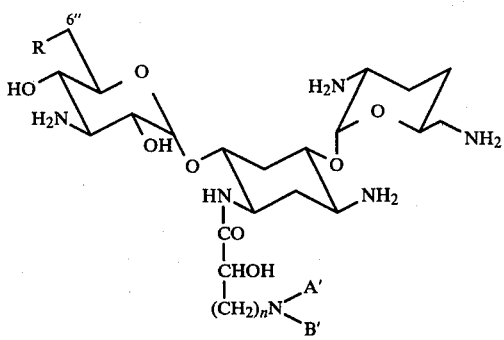

(II′)

or by the formula (II″)

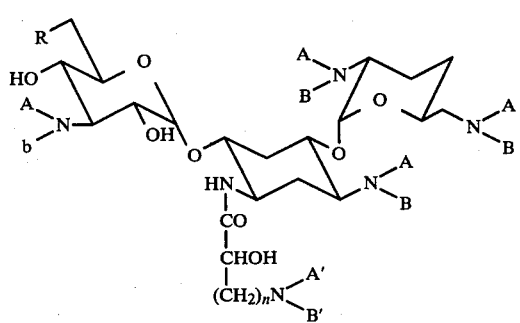

(II″)

wherein R, A, B, A′, B′ and n are as defined above, and (b) removing the remaining amino-protecting group(s) where exist(s), from the 1-N-acylated product of the formula (II′) or (II″) in a known manner to produce the compound of the formula (II).

The process of the third aspect of this invention may include a further step of converting the compound (II) into a pharmaceutically acceptable acid-addition salt thereof by reacting with a pharmaceutically acceptable inorganic or organic acid in a known manner, if desired.

The procedures for carrying out the process of the third aspect of this invention are now described in more detail.

In carrying out the present process, it is possible to employ as the starting compound 5,3′,4′-trideoxykanamycin B or 5,3′,4′,6″-tetradeoxykanamycin B (VI) of which amino groups are not protected at all, in the form of the free base or in the form of an acid-addition salt with an appropriate acid such as hydrochloric acid or sulfuric acid. However, it is preferable to employ as the starting compound such a partially amino-protected derivative of 5,3′,4′-trideoxykanamycin B or 5,3′,4′,6″-tetradeoxykanamycin B according to the formula (VI′) in which all or some of the amino groups other than the 1-amino group have been protected with known amino-protecting group(s) and which may be prepared by introduction of a known amino-protecting group into the compound of the formula (VI) by means of a known amino-protecting technique previously adopted in the synthesis of some known deoxy derivatives of kanamycin B. For the preparation of the partially amino-protected 5,3′,4′-trideoxykanamycin B or 5,3′,4′,6″-tetradeoxykanamycin B of the formula (VI′), it is feasible to utilize the amino-protecting techniques which were employed, for instance, in the preparation of the 6′-N-benzyloxycarbonyl derivative of kanamycin B as described in the specification of U.S. Pat. No. 3,781,268 or U.S. Pat. No. 3,929,762; the preparation of 2′,6′-di-N-tert-butoxycarbonyl-kanamycin B or 6′-N-benzyloxycarbonyl-kanamycin B, or the mono-N- or di-N-tert-butoxycarbonyl and even tri-N-tert-butoxycarbonyl derivative of 6′-N-benzyloxycarbonyl-kanamycin B, either isolated or in mixture thereof, as described in the specification of U.K. Pat. No. 1,426,908 or U.S. Pat. No. 3,939,143; or the preparation of 2′,3,3″,6′-tetra-N-formyl derivative of kanamycin B as described in the specification of Belgian Pat. No. 817,546.

In general, suitable examples of the amino-protecting group which may be used for the protection of some amino groups in the partially amino-protected derivative of the formula (VI′) may be an ordinary amino-protecting group, including an alkoxycarbonyl group such as tert-butoxycarbonyl and tert-amyloxycarbonyl; a cycloalkyloxycarbonyl group such as cyclohexyloxycarbonyl; an aralkyloxycarbonyl group such as benzyloxycarbonyl; an acyl group such as trifluoroacetyl and o-nitrophenoxyacetyl; a phosphinothioyl group such as diphenylphosphinothioyl and dimethylphosphinothioyl; a phosphinyl group such as diphenylphosphinyl, and the like. Preferred examples of the di-valent amino-protecting group include phthaloyl group and a group of Schiff base type such as salicylidene. The introduction of the amino-protecting group of these kinds may be conducted by reacting the compound of the formula (VI) with an appropriate known reagent for introduction of the amino-protecting group which may be in the form of an acid halide, acid azide, active ester or acid anhydride and the like, in the manner known in the conventional synthesis of peptides. By chosing the quantity of the reagent for introduction of the amino-protecting group employed in a proportion of 0.5 to 6 mol. per mol. of the compound of the formula (VI), it is possible to prepare a mixture of different, partially amino-protected derivatives (VI′) at any ratio, due to the difference in the reactivity of the respective amino groups of the compound (VI).

In the process of the third aspect of this invention, it is practical to employ as the starting compound such amino-protected 5,3′,4′-trideoxykanamycin B or 5,3′,4′,6″-tetradeoxykanamycin B derivative in which all or some of the amino groups other than the 1-amino group have or has been blocked, for example, a 3,2′,6′,3″-tetra-N-protected derivative, a 3,2′,6′-tri-N-protected derivative, a 2′,6′,3″-tri-N-protected derivative, a 2′,6′-di-N-protected derivative and a 6′-mono-N-protected derivative. Besides, a mixture of two or more of these partially N-protected derivatives may, without being purified, be used for the 1-N-acylation step of the present process.

In order to ensure that the desired product of the general formula (II) can be produced in a high yield in accordance with the process of the third aspect invention, it needs only that just the 1-amino group of the compound of the formula (VI), namely 5,3′,4′-trideoxykanamycin B or 5,3′,4′,6″-tetradeoxykanamycin B is selectively acylated with the α-hydroxy-ω-aminoalkanoic acid (VII). Accordingly, it will be evident that most preferably, a 3,2′,6′,3″-tetra-N-protected derivative of the compound (VI), that is, the amino-protected derivative of the compound (VI′) in which all the amino groups other than the 1-amino group have been blocked with the protective groups is employed as the starting compound to be 1-N-acylated in the present process.

To prepare the 3,2′,6′,3″-tetra-N-protected derivative of the formula (VI′) from the compound of the formula (VI), the following procedure may be used, for instance. Thus, there can be applied a known method of U.S. Pat. No. 4,136,254 of Nagabhushan et al by which a 3,2',6'-tri-N-acylated protected derivative of kanamycin B is prepared by reacting kanamycin B with a di-valent transition metal cation, for example, cation of copper (II), nickel (II), cobalt (II), etc. for the formation of a metal complex of kanamycin B, reacting this kanamycin B-metal complex with an acylation agent known as the amino-protecting group-introducing reagent for the protection of all the amino groups other than the 1-amino and 3"-amino groups of the kanamycin B moiety of the kanamycin B-metal complex (said 1- and 3"-amino groups having been blocked by complexing with the di-valent metal cation in the kanamycin B-metal complex), and then removing the di-valent metal cation from said complex, eg., by treatment with hydrogen sulfide or by treatment with aqueous ammonia. Or, there can be applied a method of our co-pending Japanese patent application No. 138402/78 (corresponding to our co-pending U.S. patent application Ser. No. 090,591, now U.S. Pat. No. 4,297,485; co-pending U.K. patent application No. GB 2,036,020 A; Belgian patent No. 879,925) by which a 3,2',6'-tri-N-acylated protected derivative of kanamycin B is prepared in a similar way to the aforesaid known method of Nagabhushan et al except that zinc cation is employed in stead of the di-valent transition metal cation. In this way, a 3,2',6'-tri-N-protected derivative of the formula (VI') can be prepared from the compound of the formula (VI) in a high yeild. The 3"-amino group of this 3,2',6'-tri-N-protected derivative (VI') so prepared can further be protected by the selective acylation according to a selective 3"-N-acylation method of our aforesaid co-pending Japanese patent application No. 73064/79 (see claim 15 of said Belgian Pat. No. 879,923) for the production of an amino-protected derivative of an aminoglycosidic antibiotic of which all the amino groups other than the 1-amino group have been protected selectively, so that a 3,2',6',3"-tetra-N-protected derivative of the compound (VI) can be prepared in a high yield. In accordance with the selective 3"-N-acylation method of the co-pending Japanese patent application No. 73064/79 (as described in the claim 15 of the Belgian Pat. No. 879,923), the above-mentioned 3,2',6'-tri-N-protected derivative of the compound (VI) is reacted with a formic acid alkyl ester, a di-halo- or tri-halo-alkanoic acid alkyl ester, formylimidazole or an N-alkanoyl-imidazole as the acylation agent, whereby the 3"-amino group can be acylated selectively with the acyl residue of the acylation agent employed in a high yield, without involving the acylation of the 1-amino group of said 3,2',6'-tri-N-protected derivative. The 3,2',2',3"-tetra-N-acylated derivative, for example, 3,2',6'-tri-N-benzyloxycarbonyl-3"-N-trifluoroacetyl derivative, of 5,3',4'-trideoxykanamycin B or 5,3',4',6"-tetradeoxykanamycin B which may be obtained by applying the abovementioned methods of the U.S. Pat. No. 4,136,254 and of the Belgian Pat. No. 879,923 is a most preferred starting compound to be 1-N-acylated selectively with the α-hydroxy-ω-aminoalkanoic acid (VII) in the 1-N-acylation step of the present process.

In the process of this third aspect invention, the 1-amino group of the compound of the formula (VI) or the 1-amino group of the partially amino-protected derivatives (VI') thereof, either isolated or in mixture of two or more of them, is acylated with the α-hydroxy-ω-aminoalkanoic acid of the formula (VII)

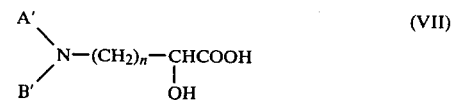

wherein A' and B' are as defined above and n is an integer of 1, 2 or 3 of which the amino group is not protected or has been protected. This α-hydroxy-ω-aminoalkanoic acid may be 3-amino-2-hydroxypropionic acid (ie. the compound of the formula (VII) where n is 1 and A' and B' are the hydrogen atoms), 4-amino-2-hydroxybutyric acid (ie. the compound of the formula (VII) where n is 2 and A' and B' are the hydrogen atoms) or 5-amino-2-hydroxyvaleric acid (ie. the compound of the formula (VII) where n is 3 and A' and B' are the hydrogen atoms). Amongst them, the (S)-isomer is preferred for use.

In the process of the third aspect invention, the 1-N-acylation with the α-hydroxy-ω-aminoalkanoic acid (VII) may be conducted according to any of one conventional methods for the synthesis of peptides, for instance, according to the known dicyclohexylcarbodi-imide method, the known mixed acid anhydride method, the known azide method or the active ester method and the like, using the α-hydroxy-ω-aminoalkanoic acid as such or in the form of its reactive derivative (as the functional equivalent thereof). For the amino-protecting group for protection of the amino group of the α-hydroxy-ω-aminoalkanoic acid may be employed such an amino-protecting group which is the same as or different from the one present in the starting compound (VI'). Particularly, a preferred amino-protecting group for this purpose is tert-butoxycarbonyl group which is easily removable by treatment with aqueous trifluoroacetic acid or acetic acid or with diluted aqueous hydrochloric acid. Benzyloxycarbonyl group which is removable by a conventional hydrogenolysis in the presence of a catalyst such as palladium or platinum oxide is a convenient N-protecting group.

The 1-N-acylation in the present process may preferably be carried out in an aqueous organic solvent according to the active ester method using and α-hydroxy-ω-aminoalkanoic acid in the form of its active ester. For example, N-hydroxysuccinimide ester of L-4-benzyloxycarbonylamino-2-hydroxybutyric acid may preferably be used as the active ester which may be prepared by a conventional method of preparing the active ester. This active ester preferably may be used in a proportion of from 0.5 to 3 molar equivalents and preferably of from 1 to 1.5 molar equivalents per mol of the starting compound (VI) or (VI') to be 1-N-acylated. The aqueous organic solvent used in the reaction medium may be a water-miscible organic solvent such as dioxane, 1,2-dimethoxyethane, dimethylformamide, tetrahydrofuran, and the like. The 1-N-acylation may be effected at ambient temperature or, if desired, at an elevated temperature of 20°-90° C. and for a reaction time of several hours and preferably of 5-6 hours.

When the 1-N-acylation in the present process is conducted using as the starting compound such as a partially amino-protected derivative in which some, but not all, of the amino groups other than the 1-amino group has or have been protected, for example, the 6'-N-protected derivative of the starting compound (VI), the acylation products as formed may partially be purified by a column chromatography, for example, on silica gel so that the unreacted starting material is removed, giving a mixture of the desired 1-N-monoacylated product with the otherwise N-acylated products, as the case be in the synthesis of habekacin, namely 1-N-[(S)-4-amino-2-hydroxybutyryl]-3',4'-dideoxykanamycin B as described in the specification of U.S. Pat. No. 4,107,424. These mixed acylation products may, without being purified and/or isolated, be subjected immediately to the subsequent de-protecting step of the present process, followed by the purification and isolation so that the desired 1-N-mono-acylated product is obtained.

In the second step of the process of this third aspect invention, the 1-N-acylation product (including the mixed acylation products) as obtained in the 1-N-acylation step of the present process is subjected to the removal of the amino-protecting groups, if these are still remaining in the 1-N-acylation product. The removal of the protecting groups is effected by a conventional deprotecting technique. Thus, the amino-protecting group of the alkoxycarbonyl type is removed by weak acid hydrolysis with an aqueous solution of trifluoroacetic acid or acetic acid and the like or with a diluted aqueous solution of an inorganic acid such as hydrochloric acid. The aralkyloxycarbonyl group such as benzyloxycarbonyl may be removed by an ordinary catalytic reduction (hydrogenolysis). When phthaloyl group is present as the amino-protecting group, it can be moved by heating in a solution of hydrazine hydrate in a lower alkanol.

The deprotected acylation product as obtained from the second, de-protecting step of the present process may contain the desired 1-N-acylation product of the formula (II) together with some isomers thereof. The desired 1-N-(α-hydroxy-ω-aminoalkanoyl) derivative (II) may be isolated and purified chromatographically using a cation-exchanger containing carboxylic functions, such as Amberlite CG-50 (a product of Rohm & Haas Co., U.S.A.) or CM-Sephadex C-25 (a product of Pharmacia Co., Sweden) and assaying the antibacterial activity of the fractions of the eluate by means of a proper kanamycin-sensitive strain and kanamycin-resistant strain of bacteria.

The 5,3',4',6"-tetradeoxykanamycin B which is used as the starting compound in the process for the production of a 1-N-(α-hydroxy-ω-aminoalkanoyl)-5,3',4',6"-tetradeoxykanamycin B in accordance with the third aspect of this invention may be prepared starting from 3',4',6"-trideoxykanamycin B already synthetized by the present inventor (this compound was referred to as 6"-deoxydibekacin in the specification of the aforesaid Japanese patent application No. 119323/79 or U.K. patent application No. GB 2 058 774 A) or an N,O-protected derivative thereof represented by the formula (VIII')

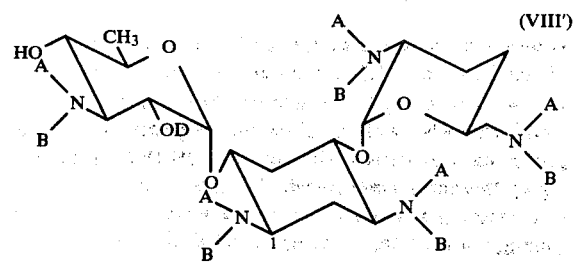

wherein A is a hydrogen atom and B is a mono-valent amino-protecting group, or A and B taken together form a di-valent amino-protecting group, and D is a hydroxyl-protecting acyl group.

According to the fourth aspect of this invention, therefore, there is provided a process for the production of 5,3',4',6"-tetradeoxykanamycin B as described hereinbefore and represented by the formula (III)

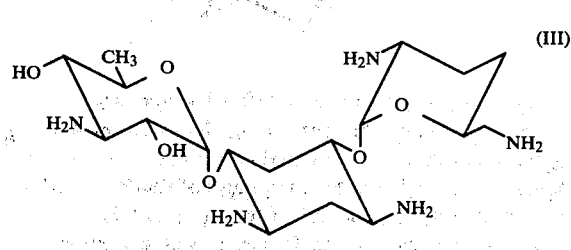

which comprises the steps of:

(a) protecting the 4"-hydroxyl group of a penta-N-protected and 2"O-protected derivative of 3'4',6"-trideoxykanamycin B represented by the formula (VIII)

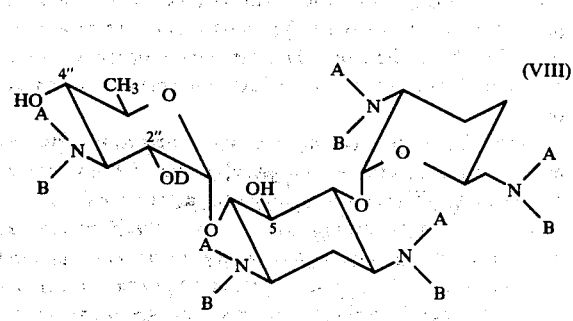

wherein A is a hydrogen atom and B is a mono-valent amino-protecting group, or A and B taken together form a di-valent amino-protecting group, and D is a hydroxyl-protecting acyl group, with a mono-valent hydroxyl-protecting acyl group of the same kind as the hydroxyl-protecting group (D) present in the 2"-position of the compound (VIII) to produce the 4"-O-protected compound of the formula (VIII')

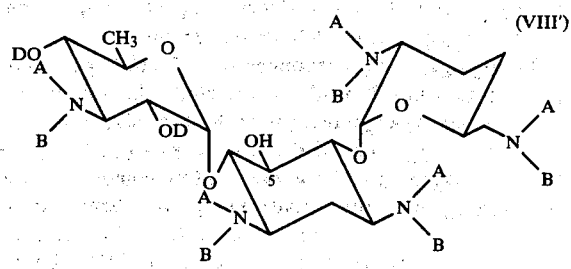

wherein A, B and D are as defined above, (b) reacting the 4"-O-protected compound of the formula (VIII') with sulfuryl chloride to replace the 5-hydroxyl group thereof with a chlorine atom to produce the corresponding 5-chloro derivative, (c) reducing the 5-chloro derivative to remove the 5-chloro group to produce a protected derivative of 5,3',4',6"-tetradeoxykanamycin B represented by the formula (IX)

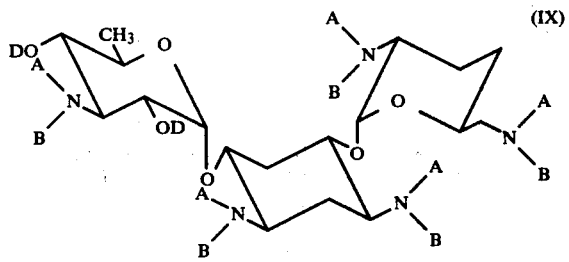

wherein A, B and D are as defined above, and (d) removing the remaining hydroxyl-protecting groups and the remaining amino-protecting groups in a known manner from the compound of the formula (IX) to produce the compound of the formula (III).

In the process of the fourth aspect invention, the amino-protecting groups present in the penta-N-protected and 2″-O-protected 3′,4′,6″-trideoxykanamycin B of the formula (VIII) employed as the starting material may be of the same kind as those present in the starting compound of the formula (VI′) which is employed in the process of the third aspect invention as described hereinbefore. The preparation of the starting compound of the formula (VIII) is described hereinafter.

In the first step of the process according to the fourth aspect invention, the 4″-hydroxyl group of the starting compound (VIII) is protected with a mono-valent hydroxyl-protecting group of acyl type which may be a lower alkanoyl group such as acetyl or an aroyl group such as benzoyl. Introduction of such hydroxyl-protecting acyl group into the 4″-hydroxyl group of the starting compound (VIII) is achieved readily by reacting the starting compound (VIII) with an appropriate acylation reagent in the form of acid anhydride, acid halide or active ester in a known manner, for example, in an organic solvent such as pyridine at a temperature of 10°-50° C., preferably at ambient temperature. Preferred acylation reagent for this purpose is acetyl chloride or benzoyl chloride. In this acylation reaction, the 5-hydroxyl group of the starting compound (VIII) is hardly acylated by the acylation reagent owing to the lower reactivity of the 5-hydroxyl group.

In this way, there is produced the 1,3,2′6′,3″-penta-N-protected and 2″,4″-di-O-protected derivative of 3′,4′,6″-trideoxykanamycin B of the formula (VIII′).

In the second step of the present process, the protected derivative (VIII′) so obtained is subjected to the deoxygenation at the 5-hydroxyl group thereof in a known manner as described in the Bulletin of the Chemical Society of Japan, Vol. 51, page 2354 (1978). Thus, the protected derivative (VIII′) is reacted with a 1 to 5 molar proportion of sulfuryl chloride in an organic solvent such as dry pyridine at a temperature lower than ambient temperature for 2 to 20 hours under agitation, affording the 5-chloro derivative.

In the third step of the present process, the 5-chloro derivative so obtained is reduced to effect the dehalogenation. This removal of the 5-chloro group may be achieved by reaction with a metal hydride such as tributyl tin hydride as described in the above-mentioned document or by conventional catalytic hydrogenation in the presence of Raney nickel. In this way, there is produced the N,O-protected derivative of 5,3′,4′,6″-tetradeoxykanamycin B of the formula (IX).

In the fourth step of the present process, the N,O-protected 5,3′,4′,6″-tetradeoxykanamycin B derivative (IX) is subjected to the deprotection. The mono-valent hydroxyl-protecting acyl groups (D) present in the 5-deoxygenated compound (IX) can easily be removed by alkaline hydrolysis at ambient temperature, for example, by dissolving the compound (IX) into ammoniac methanol (ie. a mixture of aqueous ammonia and methanol). The amino-protecting group present in the starting compound (VIII) is of the aralkyloxycarbonyl type, the amino-protecting group of this nature can be removed concurrently to the catalytic hydrogenation to which the 5-chloro derivative is subjected in the third step of the present process. The amino-protecting groups other than the aralkyloxycarbonyl group can readily be removed in a known manner, for example, by hydrolysis with weak acid. When the amino-protecting group is a lower alkoxycarbonyl group such as ethoxycarbonyl, it can be removed by alkaline hydrolysis with barium hydroxide.

In the process of the fourth aspect invention, it is possible to carry out such a modified process in which 3′,4′,6″-trideoxykanamycin B is used as the initial material, its five amino groups are protected and subsequently its two 2″- and 4″-hydroxyl groups are protected at once with the same mono-valent hydroxyl-protecting groups (D) to prepare the N,O-protected derivative of the formula (VIII′).

The preparation of the penta-N-protected and 2″-O-protected derivative of 3′,4′,6″-trideoxykanamycin B of the formula (VIII) employed as the starting compound in the process of the fourth aspect invention may be conducted as described in the specification of U.K. patent application GB 2 058 774. Thus, a pena-N-protected derivative of 3′,4′-dideoxykanamycin B represented by the formula

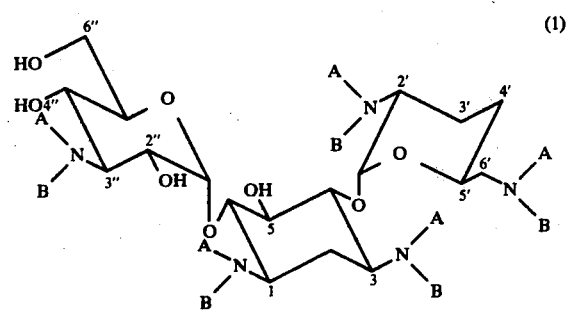

wherein A and B are as defined hereinbefore in respect of the formula (VIII) is used as the initial material, the two 4″- and 6″-hydroxyl groups thereof are protected simultaneously with a di-valent hydroxyl-protecting group such as isopropylidene group, the 2″-hydroxyl group thereof is protected with a mono-valent hydroxyl-protecting acyl group such as benzoyl and acetyl to produce a 2″,4″,6″-tri-O-protected derivative of the formula

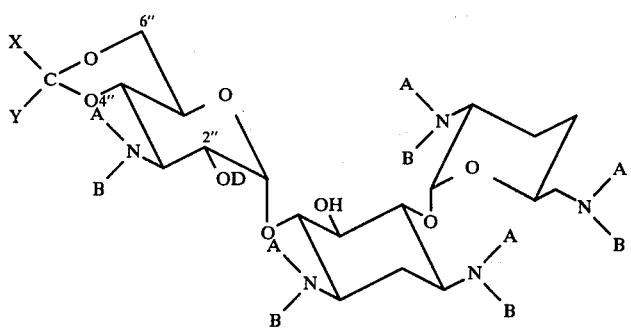
(2)

wherein A and B are as defined above, the group

is a di-valent hydroxyl-protecting group where X and Y are each a hydrogen atom, an alkyl group of 1 to 4 carbon, an aryl group such as phenyl or an alkoxyl group of 1 to 4 carbon atoms, or the group

denotes a cyclohexylidene group or a tetrahydropyranylidene group, and D is a mono-valent hydroxyl-protecting acyl group. The 2″,4″,6″-tri-O-protected derivative of the formula (2) so obtained is treated with aqueous acetic acid to remove the group

of protecting the 4″- and 6″-hydroxyl groups therefrom, and the product so partially deprotected is reacted with an appropriate sulfonylation reagent such as p-toluenesulfonyl chloride in pyridine to preferentially sulfonylate the 6″-hydroxyl group thereof and to produce a 6″-O-sulfonylated derivative of the formula

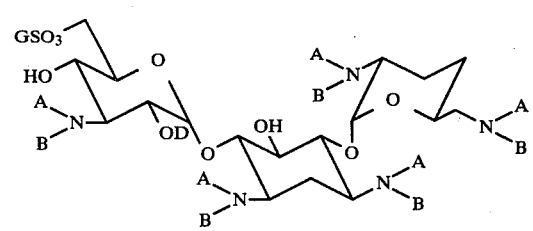
(3)

wherein A, B and D are as defined above and G is a lower alkyl group, especially an alkyl group of 1 to 4 carbon atoms, an aryl group such as phenyl or p-methylphenyl or an aralkyl group such as benzyl. The 6″-O-sulfonylated derivative obtained is then treated with an alkali metal iodide or bromide to replace the 6″-sulfonyloxy group (GSO$_3$-) by the iodo or bromo group and thereby to produce a corresponding 6″-iodo or 6″-bromo derivative (corresponding to such a compound of the formula (3) but where the group GSO$_3$- has converted into the iodine or chlorine atom), which is subsequently reduced with hydrogen in the presence of a known hydrogenation catalyst such as palladium to effect the dehalogenation, giving the penta-N-protected and 2″-O-protected 3′,4′,6″-trideoxykanamycin B derivative of the formula (VIII) as desired.

Further, the production of the new compound of the formula (IV) according to this invention is described here. Thus, the new compound of the formula (IV) such as 1-N-[(S)-4-amino-2-hydroxybutyryl]-5,3′,4′-trideoxy-6′-N-methylkanamycin B, 1-N-(3-amino-2-hydroxypropionyl)-5,3′,4′-trideoxy-6′-N-methylkanamycin B and 1-N-[(S)-5-amino-2-hydroxyvaleryl]-5,3′,4′-trideoxy-6′-N-methylkanamycin B can be synthetized by using as the starting compound the new compound 5,3′,4′-trideoxy-6′-N-methylkanamycin B as obtained in accordance with this invention and condensing the 1-amino group of this starting compound with a corresponding α-hydroxy-ω-aminoalkanoic acid or a functional equivalent thereof.

According to the fifth aspect of this invention, therefore, there is provided a process for the production of a 1-N-[α-hydroxy-ω-aminoalkanoyl]-5,3′,4′-trideoxy-6′-N-methylkanamycin B as described hereinbefore and represented by the formula (IV)

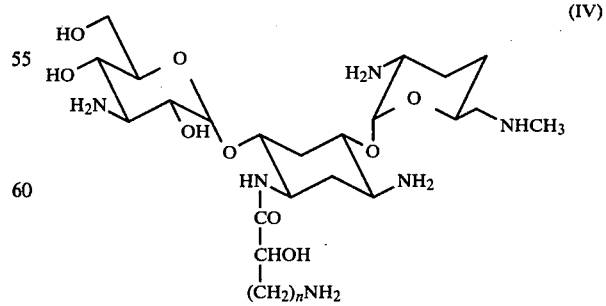
(IV)

wherein n is an integer of 1, 2 or 3, which comprises:

(a) acylating the 1-amino group of 5,3′,4′-trideoxy-6′-N-methylkanamycin B represented by the formula (V)

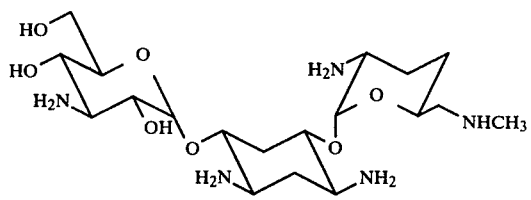

(V)

or a partially amino-protected derivative of 5,3',4'-trideoxy-6'-N-methylkanamycin B represented by the formula (V')

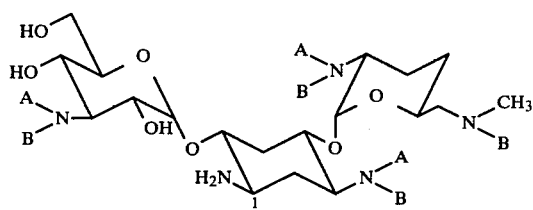

(V')

wherein A is a hydrogen atom and at least one B is a mono-valent amino-protecting group but the other B(s) is or are each a hydrogen atom, or at least one pair of A and B taken together form a di-valent amino-protecting group but the other A and B are each a hydrogen atom, and the amino-protecting groups represented by A and B may be equal to each other or different from each other, by reaction with an α-hydroxy-ω-aminoalkanoic acid or an amino-protected derivative thereof represented by the formula (VII)

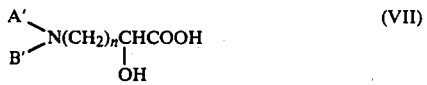

(VII)

wherein A' is a hydrogen atom and B' is a hydrogen atom or a mono-valent amino-protecting group, or A' and B' taken together form a di-valent amino-protecting group and n is an integer of 1, 2 or 3, or a functional equivalent of the compound (VII), to produce the 1-N-acylated product represented by the formula (IV')

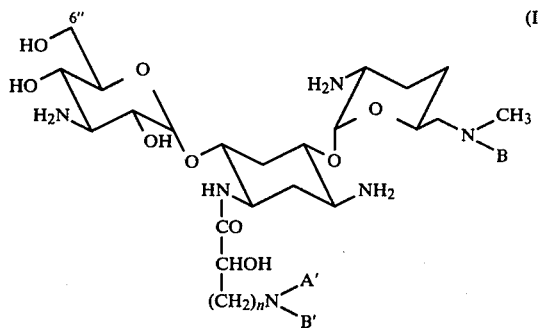

(IV')

or by the formula (IV")

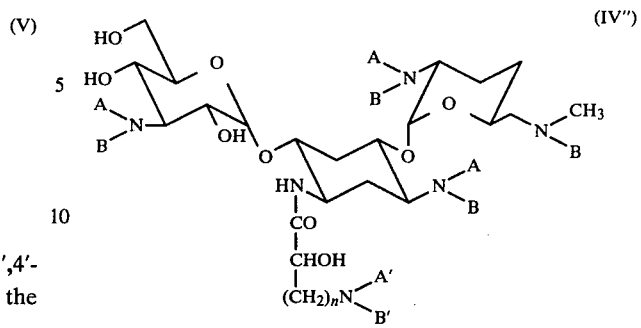

(IV")

wherein A, B, A', B' and n are as defined above, and (b) removing the remaining amino-protecting group(s) where exist(s) from the 1-N-acylated product of the formula (IV') or (IV") in a known manner to produce the compound of the formula (IV).

The process of the fifth aspect of this invention may include a further step of converting the compound (VI) as produced into a pharmaceutically acceptable acid-addition salt thereof by reacting with a pharmaceutically acceptable inorganic or organic acid in a known manner, if desired.

The process of the fifth aspect invention can be carried out in the same manner as described hereinbefore for the process of the third aspect of this invention.

In carrying out the process of the fifth aspect invention, it is feasible to employ as the starting compound 5,3',4'-trideoxy-6'-N-methylkanamycin B of the formula (V) of which amino groups are not protected at all, in the form of the free base or in the form of an acid-addition salt with an appropriate acid such as hydrochloric acid. However, it is preferred to employ as the starting compound such a partially amino-protected derivative of 5,3',4'-trideoxy-6'-N-methylkanamycin B according to the formula (V') in which all or some of the three amino groups and methylamino group other than the 1-amino group have been protected with known amino-protecting groups and which may be prepared by introduction of a known amino-protecting group into the compound (V) as described detailedly in respect to the process of the third aspect invention.

In the process of the fifth aspect invention, the step of 1-N-acylating the starting compound (IV) or (IV') and the step of deprotecting the 1-N-acylated product (IV') or (IV") as well as the step of purifying the deprotected 1-N-acylation product are worked out just as described hereinbefore in respect of the corresponding steps of the process of the third aspect invention.

The new compound of the formula (V), namely 5,3',4'-tri-deoxy-6'-N-methylkanamycin B which is used as the starting compound in the process of the aforesaid fifth aspect invention may be prepared starting from a known compound, 5,3',4'-trideoxykanamycin B (Japanese Journal of Antibiotics, Vol. 32, S-178 (1979) and conducting N-methylation at the 6'-amino group of said starting compound in the same manner as described in Japanese patent application No. 83671/72, U.S. Pat. No. 3,925,353 or the "Journal of Antibiotics" 25, 743 (1972).

According to the sixth aspect of this invention, there is provided a process for the production of 5,3',4'-trideoxy-6'-N-methylkanamycin B represented by the formula (V)

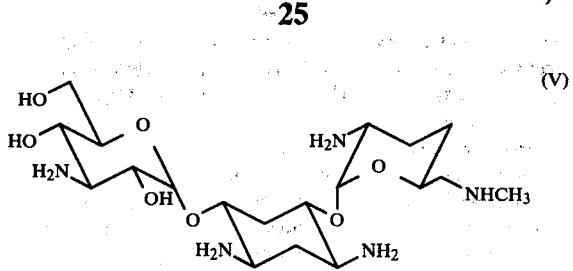

which comprises the steps of:

(a) introducing an alkyloxycarbonyl group, a cycloalkyloxycarbonyl group or an aralkyloxycarbonyl group into the 6'-amino group of 5,3',4'-trideoxykanamycin B represented by the formula (X)

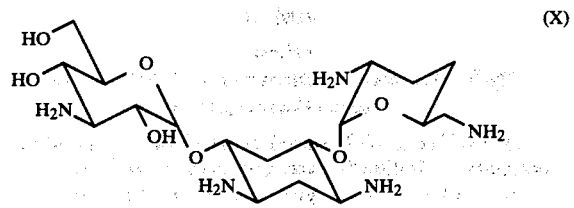

to produce the compound of the formula (XI)

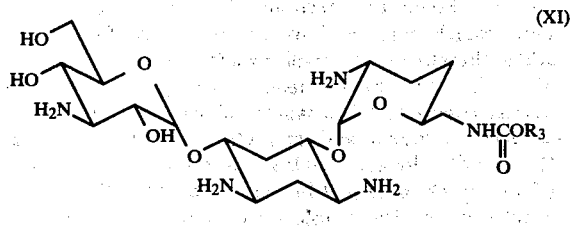

wherein $R_3$ is an alkyl group of 1 to 6 carbon atoms, a cycloalkyl group of 3 to 6 carbon atoms or an aralkyl group, particularly a phenyl-($C_1$-$C_4$)alkyl group, especially benzyl, and (b) reducing the compound of the formula (XI) with a metal hydride in an anhydrous organic solvent to produce the compound of the formula (V).

The procedures for carrying out the process of the sixth aspect invention are now described.

In the first step of the present process, an alkyloxycarbonyl group, a cycloalkyloxycarbonyl group or aralkyloxycarbonyl group is introduced into the 6'-amino group of the starting compound (X) and may be the one which is usually known as the amino-protecting group of urethane type. Introduction of the alkyloxycarbonyl, cycloalkyloxycarbonyl or aralkyloxycarbonyl group

into the 6'-amino group of the starting 5,3',4'-trideoxykanamycin B (X) is achieved in the same manner as described hereinbefore for the preparation of the amino-protected derivative of the starting material (VI') which is employed in the process of the third aspect invention. The selective protection of the 6'-amino group can be made because the 6'-amino group is most reactive amongst the amino groups of the kanamycin B compound (X). The group $$(-COR_3) \atop \| \atop O$$

to be intorduced into the 6'-amino group of the starting compound (X) may preferably be methoxycarbonyl group, ethoxycarbonyl group or benzyloxycarbonyl group. In this way, the 6'-N-alkyloxycarbonylated, 6'-N-cycloalkyloxycarbonylated or 6'-N-aralkyloxycarbonylated product of the formula (XI) is formed.

The 6'-N-alkyloxycarbonyl group, 6'-N-cycloalkyloxycarbonyl group or 6'-N-aralkyloxycarbonyl group so introduced is reductively converted into a methyl group to effect the 6'-N-methylation. This can be achieved by reducing the compound of the formula (XI) with a metal hydride such as lithium aluminum hydride and diborane in an anhydrous organic solvent such as tetrahydrofuran. This reduction may usually be carried out at a temperature of 40°-90° C. for 10 hours or longer.

This invention is illustrated with reference to the following Examples to which this invention is not limited. Examples 1 to 3 are illustrative of the first and third aspects of this invention, Example 4 illustrative of the first and fourth aspects of this invention, Example 5 illustrative of the sixth aspect of this invention, and Examples 6-8 illustrative of the fifth aspect of this invention.

EXAMPLE 1

Synthesis of 1-N-[(S)-4-amino-2-hydroxybutyryl]-5,3',4'-trideoxykanamycin B (a) 4.36 g (10 mmole) of 5,3',4'-trideoxykanamycin B was dissolved in 100 ml of dry dimethylsulfoxide, to which was then added 10.5 g (48 mmole) of zinc acetate [$Zn(CH_3CO_2)_2.2H_2O$]. The resultant mixture was agitated at ambient temperature for 20 hours to form a complex of 5,3',4'-trideoxykanamycin B with zinc cation. After addition of 12.0 g (39.5 mmole) of paramethoxybenzyl S-4,6-dimethylpryrimid-2-ylthiocarbonate (product of Kokusan Kagaku K.K., Japan), the resultant admixture was agitated at 50° C. for 7.5 hours to effect the N-p-methoxybenzyloxycarbonylation. The reaction solution obtained was then poured into 1000 ml of water and adjusted to pH 11 by addition of aqueous ammonia to effect the breakdown of the zinc complex, giving a precipitate. The precipitate was filtered off, washed with 500 ml of water and dissolved in 60 ml of a mixed solvent of chloroform-methanol-17% aqueous ammonia (50:10:1 by volume). The solution was subjected to chromatography on a column of 500 g of silica gel (Wako-gel C-200) developing with the same mixed solvent to give 4.1 g (44%) of a colorless powder of 3,2',6'-tri-N-paramethoxybenzyloxycarbonyl-5,3',4'-trideoxykanamycin B.

3.7 g (4 mmole) of the colorless powder was dissolved in 50 ml of dimethylsulfoxide and 0.95 ml (8 mmole) of ethyl trifluoroacetate was added to the solution. The resulting mixture was stirred at room temperature for 5 hours to effect the 3"-N-trifluoroacetylatoin and yield 3,2',6'-tri-N-paramethoxybenzyloxycarbonyl-3"-N-trifluoroacetyl-5,3',4'-trideoxykanamycin B.

(b) To the reaction solution containing the N-protected kanamycin B derivative obtained in step (a) above were added 0.6 ml (4.4 mmole) of triethylamine, followed by a solution of 1.9 g (6 mmole) of N-hydroxysuccinimide ester of (S)-4-tert-butoxycarbonylamino-2-hydroxybutyric acid in 20 ml of dioxane. The mixture was agitated at room temperature for 19 hours, after which the reaction solution was poured into 500 ml of water to separate a precipitate. The precipitate was filtered off and washed with 100 ml of water to give 10.9 g of a colorless powder. The powder was dissolved in 20 ml of 90% trifluoroacetic acid and the solution was allowed to stand at ambient temperature for 45 minutes to perform removal of the amino-protecting groups. The solution was then concentrated to dryness and the residue was taken up in 100 ml of water. The aqueous solution was adjusted to pH 10.5 by addition of aqueous ammonia and stirred at ambient temperature for 20 hours to permit removal of the trifluoroacetyl group. The resultant reaction solution was concentrated to a volume of about 20 ml, adjusted to pH 7.5 by addition of aqueous ammonia, diluted with 50 ml of water and then passed through a column of 150 ml of Amberlite CG-50 resin ($NH_4$ form, product of Rohm & Haas Co., U.S.A.). The column was washed successively with 750 ml of water and with 500 ml of 0.5 N aqueous ammonia and then eluted with 0.8 N aqueous ammonia. The eluate fractions containing the desired product were combined together and concentrated to dryness to give 1.76 g (72%) of 1-N-[(S)-4-amino-2-hydroxybutyryl]-5,3',4'-trideoxykanamycin B monocarbonate monohydrate as a colorless powder. Overall yield 32%.

EXAMPLE 2

Synthesis of 1-N-(3-amino-2-hydroxypropionyl)-5,3',4'-trideoxykanamycin B (a) 435.5 mg (1 mmole) of 5,3',4'-trideoxykanamycin B was dissolved in 10 ml of dry dimethylsulfoxide, to which was then added 1.05 g (4.8 mmole) of zinc acetate [$Zn(CH_3CO_2)_2.2H_2O$]. The resulting mixture was agitated at room temperature for 23 hours. Thereafter, a solution of 937.3 mg (3.9 mmole) of tert-butyl S-4,6-dimethylpyrimid-2-ylthiocarbonate in 5 ml of dimethylsulfoxide was added thereto and the resulting admixture was stirred at 50° C. for 24 hours to effect the N-tert-butoxycarbonylation. The reaction solution obtained was admixed with 15 ml of water, adjusted to pH 11 with aqueous ammonia, followed by addition of 6.4 g of sodium chloride and extraction with ethyl acetate (2×15 ml). The ethyl acetate extracts were combined together and concentrated to dryness and the residue was taken up in 6 ml of dimethylsulfoxide. The solution was admixed with 0.125 ml (1 mmole) of ethyl trifluoroacetate and the admixture was stirred at ambient temperature for 4 hours to effect the 3"-N-trifluoroacetylation.

(b) To the reaction solution containing 3,2',6'-tri-N-tert-butoxycarbonyl-3"-trifluoroacetyl-5,3',4'-trideoxykanamycin B produced in step (a) above were added 0.1 ml (0.7 mmole) of triethylamine and 384 mg (1.05 mmole) of N-hydroxysuccinimide ester of paramethoxybenzyloxycarbonylisoserine. The resultant mixture was agitated at ambient temperature for 20 hours, after which the reaction solution was admixed with 10 ml of water and extracted with ethyl acetate (2×10 ml). The combined extracts were concentrated to a small volume, followed by addition of 20 ml of 3 N hydrochloric acid—50% methanol. The mixture was stirred at room temperature for 2 hours to perform simultaneous removal of both the tert-butoxycarbonyl and para-methoxybenzyloxycarbonyl groups as the amino-protective groups. The resulting reaction solution was adjusted to pH 10 by addition of aqueous ammonia and then stirred at ambient temperature for 21 hours to permit removal of the trifluoroacetyl group. The reaction solution so obtained was evaporated to a small volume and diluted with water, and the resulting aqueous solution was passed through a column of 25 ml of Diaion WK-10S ($NH_4^+$ form, product of Mitsubishi Kasei K.K., Japan). The column was washed with 125 ml of water and then eluted with 0.4 N aqueous ammonia. The eluate fractions containing the desired product were combined together and concentrated to dryness to give 257 mg of 1-N-(3-amino-2-hydroxypropionyl)-5,3',4'-trideoxykanamycin B monocarbonate as a colorless powder. Overall yield 42%.

EXAMPLE 3

Synthesis of 1-N-[(S)-4-amino-2-hydroxybutyryl]-5,3',4',6"-tetradeoxykanamycin B (a) 419.5 mg (0.75 mmole) of 5,3',4',6"-tetradeoxykanamycin B dicarbonate monohydrate was dissolved in 10 ml of dry dimethylsulfoxide, to which was then added 1.05 g (4.8 mmole) of zinc acetate [$Zn(CH_3CO_2)_2.2H_2O$] and the mixture was agitated at room temperature for 18 hours. Thereafter, a solution of 1.44 g (6.0 mmole) of tert-butyl S-4,6-dimethylpyrimid-2-ylthiocarbonate in 5 ml of dimethylsulfoxide was added thereto and the resulting admixture was stirred at 50° C. for 25 hours. The reaction solution obtained was admixed with 15 ml of water, adjusted to pH 11 with aqueous ammonia and extracted with ethyl acetate (2×15 ml). The aqueous layer was admixed with 6.4 g of sodium chloride and further extracted with 20 ml of ethyl acetate. The whole ethyl acetate extracts were combined together and concentrated to dryness and the residue was taken up in 6 ml of dimethylsulfoxide. The solution was admixed with 0.125 ml (1 mmole) of ethyl trifluoroacetate and the admixture was stirred at ambient temperature for 4 hours.

(b) To the reaction solution containing 3,2',6'-tri-N-tert-butoxycarbonyl-3"-N-trifluoroacetyl-5,3',4',6"-tetradeoxykanamycin B produced in step (a) above were added 0.1 ml (0.7 mmole) of triethylamine and 399.4 mg (1.05 mmole) of N-hydroxysuccinimide ester of (S)-4-p-methoxybenzyloxycarbonylamino-2-hydroxybutyric acid. The resultant mixture was agitated at ambient temperature for 18 hours, after which the reaction solution was admixed with 10 ml of water and extracted with ethyl acetate (2×10 ml). The combined extracts were concentrated to a small volume, followed by addition of 20 ml of 3 N hydrochloric acid—50% methanol. The mixture was stirred at room temperature for 2 hours to perform removal of both the tert-butoxycarbonyl and para-methoxybenzyloxycarbonyl groups. The resulting reaction solution was adjusted to pH 10 by addition of aqueous ammonia and then stirred at ambient temperature for 20 hours to permit removal of the trifluoroacetyl group. The reaction solution so obtained was evaporated to a small volume and diluted with water, and the resulting aqueous solution was passed through a column of 25 ml of Diaion WK-10S ($NH_4$ form). The column was washed with 125 ml of water and then eluted with 0.32 N aqueous ammonia. The eluate fractions containing the desired product were combined together and concentrated to dryness to give 303 mg of 1-N-[(S)-4-amino-2-hydroxybutyryl]-5,3',4',6"-tetradeoxykanamycin B dicarbonate as a colorless powder. Overall yield 63%.

EXAMPLE 4

Synthesis of 5,3',4',6"-tetradeoxykanamycin B (a) Preparation of 1,3,2',6',3"-penta-N-ethoxycarbonyl-3',4'-dideoxykanamycin B 4.64 g (10.3 mmole) of 3',4'-dideoxykanamycin B was disolved in a mixture of 45 ml of water and 45 ml of methanol, to which was then added 8 g (95.2 mmole) of sodium bicarbonate, followed by slow addition of 7.2 ml (75.6 mmole) of ethyl chloroformate under ice-cooling. The resultant mixture was stirred at room temperature for 18 hours to effect the N-ethoxycarbonylation. The reaction solution obtained was admixed with 500 ml of water to separate a precipitate. The latter was filtered off and washed with water to afford 6.49 g (78%) of a colorless powder of the title compound.

(b) Preparation of 1,3,2',6',3"-penta-N-ethoxycarbonyl-4",6"-O-isopropylidene-3',4'-dideoxykanamycin B 4.83 g (5.95 mmole) of the product obtained in step (a) above was dissolved in 50 ml of dimethylformamide, and to the resulting solution were added 30 mg (0.16 mmole) of p-toluenesulfonic acid and 1.1 ml (9.0 mmole) of 2,2-dimethoxypropane. The resulting mixture was agitated at ambient temperature for 25 hours (to effect the 4",6"-O-isopropylidenation), after which the reaction solution was admixed with 1 ml (7.2 mmole) of triethylamine and then concentrated to dryness to give 5.1 g (100%) of the title compound as a pale yellow powder.

(c) Preparation of 1,3,2',6',3"-penta-N-ethoxycarbonyl-4",6"-O-isopropylidene-2"-O-benzoyl-3',4'-dideoxykanamycin B 5.1 g (6.0 mmole) of the product from step (b) above was dissolved in 75 ml of pyridine, to which was then added 1 ml (8.6 mmole) of benzoyl chloride, and the mixture was agitated at room temperature for 5 hours to effect the 2"-O-benzoylation. The reaction solution so obtained was admixed with 10 ml of water, stirred at room temperature and then concentrated to dryness. The residue was taken up in 250 ml of chloroform and the solution was washed successively with 100 ml of 0.2 N hydrochloric acid and 2×100 ml of saturated aqueous sodium bicarbonate solution. The chloroform layer was separated, dried over anhydrous sodium sulfate and concentrated to dryness to give 5.7 g (99%) of the title compound as a pale yellow powder.

(d) Preparation of 1,3,2',6',3"-penta-N-ethoxycarbonyl-2"-O-benzoyl-3',4'-dideoxykanamycin B 5.3 g (5.5 mmole) of the product from step (c) above was dissolved in 80 ml of a mixture of acetic acid-methanol-water (2:1:1 by volume) and the resultant solution was allowed to stand at ambient temperature for 21 hours and then concentrated to dryness to yield 4.9 g (97%) of the title compound as a pale yellow powder.

(e) Preparation of 1,3,2',6',3"-penta-N-ethoxycarbonyl-2"-O-benzoyl-6"-O-tosyl-3',4'-dideoxykanamycin B 1.5 g (1.63 mmole) of the product obtained in step (d) above was dissolved in 28 ml of pyridine, to which was then added 374 mg (1.96 mmole) of paratoluenesulfonyl chloride, and the mixture was agitated at room temperature for 28 hours to effect the 6"-O-tosylation. The resulting reaction solution was concentrated to dryness, the powdery residue (2.3 g) was taken up in 12.5 ml of dichloromethane and the solution obtained was subjected to column chromatography on silica gel (Wako-gel C-200, 200 g). The column was washed with 100 ml of dichloromethane-ethanol (60:1) and then developed with dichloromethane-ethanol (50:1) to give 1.0 g (60%) of a colorless powder of the title compound.

(f) Preparation of 1,3,2',6',3"-penta-N-ethoxycarbonyl-2"-O-benzoyl-6"-iodo-3',4'-dideoxykanamycin B 900 mg (0.84 mmole) of the product from step (e) above was dissolved in 18 ml of dimethylformamide, followed by addition of 12.6 g (84 mmole) of sodium iodide and agitation at 95° C. for two hours to effect the 6"-iodination. The reaction solution obtained was poured into 250 ml of water, and the precipitate deposited was filtered off and then dissolved in 100 ml of chloroform. The chloroform solution was washed with 100 ml of 20% aqueous sodium thiosulfate and with 100 ml of saturated aqueous sodium chloride. The chloroform layer separated was dried over anhydrous sodium sulfate and concentrated to dryness to give 817 mg (95%) of the title compound as a colorless powder.

(g) Preparation of 1,3,2',6',3"-penta-N-ethoxycarbonyl-2"-O-benzoyl-3',4',6"-trideoxykanamycin B 773 mg (0.75 mmole) of the product from step (f) above was dissolved in 20 ml of dioxane, to which was then added a small amount of Raney Nickel W-2, and the mixture was hydrogenated under a hydrogen pressure of 3.6 kg/cm$^2$ for 23.5 hours using a Parr apparatus. The resultant reaction solution was filtered to remove the catalyst and then concentrated to dryness to afford 655 mg (97%) of a colorless powder of the title compound.

(h) Preparation of 1,3,2',6',3"-penta-N-ethoxycarbonyl-2",4"-di-O-benzoyl-3',4',6'-trideoxykanamycin B 622 mg (0.69 mmole) of the product obtained in step (g) above was dissolved in 30 ml of pyridine, followed by addition of 0.1 ml (0.86 mmole) of benzoyl chloride and agitation of the mixture at room temperature for 25 hours to effect the 4"-O-benzoylation. The resultant reaction solution was concentrated to dryness and the residue was taken up in 50 ml of chloroform. The solution was washed successively with 10% aqueous potassium bisulfate (2×30 ml), saturated aqueous sodium bicarbonate (2×30 ml) and saturated aqueous sodium chloride (1×30 ml), then dried over anhydrous sodium sulfate and concentrated to dryness to give 663 mg (96%) of the title compound as a colorless powder.

(i) Preparation of 1,3,2',6',3"-penta-N-ethoxycarbonyl-2",4"-di-O-benzoyl-5-chloro-3',4',6"-trideoxykanamycin B 600 mg (0.6 mmole) of the product from step (h) above was dissolved in 12 ml of pyridine, to which was then added 0.1 ml (1.24 mmole) of sulfuryl chloride under ice-cooling, and the mixture was stirred at ambient temperature for 18 hours to effect the 5-chlorination. The reaction solution thus obtained was admixed with 100 ml of water and extracted with 60 ml of chloroform. The chloroform extract was washed successively with 60 ml of 10% aqueous potassium bisulfate, 60 ml of saturated aqueous sodium bicarbonate and 60 ml of saturated aqueous sodium chloride, then dried over anhydrous sodium sulfate and concentrated to dryness. The resultant powdery residue (572 mg) was taken up in 5 ml of dichloromethane and chromatographed on a column of silica gel (Wako-gel C-200, 50 g). The column was washed with 500 ml of dichloromethane and developed with a mixture of dichloromethane-ethanol (100:1) to give 356 mg (58%) of a colorless powder of the title compound.

(j) Preparation of 1,3,2',6',3''-penta-N-ethoxycarbonyl-2'',4''-di-O-benzoyl-5,3',4',6''-tetradeoxykanamycin B 308 mg (0.13 mmole) of the product from step (i) above was dissolved in 5 ml of dioxane, to which was then added a small amount of Raney Nickel W-2, and the mixture was hydrogenated under a hydrogen pressure of 3.6 kg/cm$^2$ for 23.5 hours using a Parr apparatus to effect the dechlorination. The resultant reaction solution was filtered to remove the catalyst and then concentrated to dryness to afford 295 mg (100%) of a colorless powder of the title compound.

(i) Preparation of 5,3',4',6''-tetradeoxykanamycin B 120 mg (0.12 mmole) of the product obtained in step (j) above was dissolved in a mixture of 1 ml of dioxane and 1 ml of water, to which was then added 400 mg (1.27 mmole) of barium hydroxide [Ba(OH$_2$).8H$_2$O], and the resultant mixture was subjected to the deprotection by heating at 110° C. for 15 hours under reflux. Thereafter, gaseous carbon dioxide was passed into the reaction solution to precipitate barium carbonate, which was filtered off. The filtrate was admixed with 30 ml of water and passed through a column of 20 ml of Amberlite CG-50 (NH$_4$ form, product of Rohm & Haas Co., U.S.A.). The column was washed with 100 ml of water and 75 ml of 0.1 N aqueous ammonia and then eluted with 0.3 N aqueous ammonia. The eluate fractions containing the desired product were combined together and concentrated to dryness to give 19.5 mg (29%) of 5,3',4',6''-tetradeoxykanamycin B dicarbonate monohydrate as a colorless powder.

EXAMPLE 5

Synthesis of 5,3',4'-trideoxy-6'-N-methylkanamycin B (a) 4.0 g (9.18 mmole) of 5,3',4'-trideoxykanamycin B was dissolved in a mixture of 40 ml of water and 40 ml of methanol, to which was then added a solution of 5.8 ml (9.18 mmole) of triethylamine and 2.72 g (11.02 mmole) of 2-(tert-butoxycarbonyloxyimino)-2-phenylacetonitrile (commercially available under the name of BOC-ON from Aldrich Co., U.S.A.) in 40 ml of methanol. The resultant mixture was agitated at room temperature for 3 hours, after which the reaction solution containing 6'-N-tert-butoxycarbonyl-5,3',4'-trideoxykanamycin B formed was admixed with 2 ml of 17% aqueous ammonia and concentrated to dryness. The residue was taken up in 100 ml of water and the solution was adjusted to pH 7.4 with 6 N hydrochloric acid, washed with 50 ml of ethyl ether and then passed through a column (20 mm in inner diameter) of 100 ml of Amberlite CG-50 (NH$_4$+ form, product of Rohm & Haas Co., U.S.A.). The column was washed with 300 ml of water and 150 ml of 0.1 M aqueous ammonia and then eluted with 0.2 M aqueous ammonia. The eluate was collected in 5 ml-fractions and the fractions No. 11-24 were combined together and concentrated to dryness to give 2.1 g (42.5%) of 6'-N-tert-butoxycarbonyl-5,3',4'-trideoxykanamycin B. Concentration to dryness of the fractions No. 26-33 combined recovered 1.42 g (35.6%) of unreacted 5,3',4'-trideoxykanamycin B.

(b) 1.86 g (3.45 mmole) of the 6'-N-tert-butoxycarbonyl-5,3',4'-trideoxykanamycin B obtained just above was dissolved in 60 ml of dry tetrahydrofuran, followed by addition of 1.31 g (34.5 mmole) of lithium aluminium hydride and heating at 80° C. for 20 hours under reflux. The resulting reaction mixture was added dropwise into 200 ml of water to separate a precipitate, which was filtered off. The filtrate was evaporated to remove the tetrahydrofuran and then adjusted to pH 6.5 by addition of hydrochloric acid. The solution so obtained was passed through a column (12 mm in inner diameter) of 30 ml of Amberlite CG-50 (NH$_4$+) and the column was washed with 150 ml of water and eluted successively with 0.2 M aqueous ammonia (150 ml), 0.3 M aqueous ammonia (150 ml) and 0.4 M aqueous ammonia. The eluate was collected in 6 ml-fractions and the fractions No. 11-17 were combined together and concentrated to dryness to recover 740 mg (39.9%) of unreacted 6'-N-tert-butoxycarbonyl-5,3',4'-trideoxykanamycin B. While, the fractions No. 37-55 were likewise concentrated to dryness to afford 592 mg (32.4%) of the title compound 5,3',4'-trideoxy-6'-N-methylkanamycin B.

EXAMPLE 6

Synthesis of 1-N-[(S)-4-amino-2-hydroxybutyryl]-5,3',4'-trideoxy-6'-N-methylkanamycin B 583 mg (1.10 mmole) of the 5,3',4'-trideoxy-6'-N-methylkanamycin B prepared as described in Example 5 was dissolved in 10 ml of 90% aqueous dimethylsulfoxide, to which was then added 1.16 g (5.28 mmole) of zinc acetate [Zn(CH$_3$CO$_2$)$_2$.2H$_2$O]. The mixture was stirred at ambient temperature for 20 hours, followed by addition of a solution of 1.06 g (4.29 mmole) of 2-(tert-butoxycarbonyloxyimino)-2-phenylacetonitrile in 5 ml of dimethylsulfoxide and further agitation at 50° C. for 6 hours to effect the N-tert-butoxycarbonylation. The resulting reaction solution was admixed with 2 ml of 17% aqueous ammonia and then with 100 ml of water and washed with 50 ml of ethyl ether. The aqueous layer separated was adjusted to pH 11 with 17% aqueous ammonia and admixed with 2 g of sodium chloride, and the resulting solution was extracted with ethyl acetate (3×100 ml). The ethyl acetate extracts combined were dried over anhydrous sodium sulfate and concentrated to dryness. The residue was chromatographed on a column (20 mm in inner diameter) of 50 g of silica gel (Wako-gel C-200 manufactured by Wako Junyaku K.K., Japan) using as the eluent a mixture of chloroform-methanol-conc. aqueous ammonia (30:10:1 by volume). The eluate was collected in 10 ml-fractions and the fractions No. 25-50 were combined together and concentrated to dryness to give 607 mg (73.6%) of 3,2',6'-tri-N-tert-butoxycarbonyl-5,3',4'-trideoxy-6'-N-methylkanamycin B.

590 mg (0.787 mmole) of the product obtained just above was dissolved in 10 ml of dimethylsulfoxide, and to the solution obtained was added 0.14 ml (1.18 mmole) of ethyl trifluoroacetate. The admixture was stirred at room temperature for 1.5 hours to effect the 3''-N-trifluoroacetylation. The resultant reaction solution containing 3,2',6'-tri-N-tert-butoxycarbonyl-3''-N-trifluoroacetyl-5,3',4'-trideoxy-6'-N-methylkanamycin B produced was admixed with both 0.16 ml (1.18 mmole) of triethylamine and 420 mg (1.18 mmole) of N-hydroxysuccinimide ester of (S)-4-p-methoxybenzyloxycarbonylamino-2-hydroxybutyric acid dissolved in 4 ml of tetrahydrofuran and the admixture was agitated at room temperature for 4 hours to effect the 1-N-acylation. Subsequently, 100 ml of water was added to the reaction solution, which was then extracted with ethyl acetate (2×100 ml). The extracts combined were dried over anhydrous sodium sulfate and concentrated to dryness to afford the 1-N-acylated product in the form of the amino-protected derivative thereof.

This 1-N-acylated product so obtained was dissolved in 10 ml of 90% aqueous trifluoroacetic acid and the solution was agitated at ambient temperature for 5 hours to permit the removal of the tert-butoxycarbonyl and p-methoxybenzyloxycarbonyl groups and then the reaction solution was concentrated to dryness. The residue was taken up in 30 ml of water and the solution was adjusted to pH 10 with 17% aqueous ammonia, followed by stirring at room temperature for 18 hours to permit the removal of the trifluoroacetyl group. The reaction solution thus obtained was adjusted to pH 7.5 by addition of 6 N hydrochloric acid and passed through a column (13 mm in inner diameter) of 20 ml of Amberlite CG-50 ($NH_4^+$ form). The column was washed with 100 ml of water and eluted successively with 160 ml of 0.5 M aqueous ammonia and 100 ml of 0.8 M aqueous ammonia. The eluate was collected in 4 ml-fractions and the fractions No. 27–62 were combined together and concentrated to dryness to yield 346 mg (71.8%) of the titled compound, 1-N-[(S)-4-amino-2-hydroxybutyryl]-5,3′,4′-trideoxy-6′-N-methylkanamycin B in the form of its monocarbonate.

EXAMPLE 7

Synthesis of 1-N-[3-amino-2-hydroxypropionyl]-5,3′,4′-trideoxy-6′-N-methylkanamycin B 102 mg (0.136 mmole) of the 3,2′,6′-tri-N-tert-butoxycarbonyl-5,3′,4′-trideoxy-6′-N-methylkanamycin B prepared as in Example 6 was dissolved in 3 ml of dimethylsulfoxide, and to the resultant solution was added 0.02 ml (0.204 mmole) of ethyl trifluoroacetate. The mixture was stirred at room temperature for one hour. The resultant reaction solution containing 3,2′,6′-tri-N-tert-butoxycarbonyl-3″-N-trifluoroacetyl-5,3′,4′-trideoxy-6′-N-methylkanamycin B produced was admixed with both 0.03 ml (0.204 mmole) of triethylamine and 75 mg (0.204 mmole) of N-hydroxysuccinimide ester of 3-p-methoxybenzyloxycarbonylamino-2-hydroxypropionic acid dissolved in 0.5 ml of tetrahydrofuran, and the admixture was agitated at room temperature for 7 hours to effect the 1-N-acylation. Subsequently, 10 ml of water was added to the reaction solution, which was then extracted with ethyl acetate (2×10 ml). The extracts combined were dried over anhydrous sodium sulfate and concentrated to dryness to afford 136 mg of the 1-N-acylated product in the form of the amino-protected derivative thereof.

This 1-N-acylated product was dissolved in 3 ml of 90% aqueous trifluoroacetic acid and the solution was agitated at ambient temperature for 2 hours to permit the removal of the tert-butoxycarbonyl and p-methoxybenzyloxycarbonyl groups, and then the reaction solution was concentrated to dryness. The residue was taken up in 10 ml of water and the solution was adjusted to pH 10 with 17% aqueous ammonia, followed by stirring at room temperature for 16 hours to permit the removal of the trifluoroacetyl group. The reaction solution thus obtained was adjusted to pH 6.4 by addition of 6 N hydrochloric acid and passed through a column (11 mm in inner diameter) of 10 ml of Amberlite CG-50 ($NH_4^+$ form). The column was washed with 30 ml of water and 30 ml of 0.2 M aqueous ammonia and then eluted with 0.5 M aqueous ammonia. The eluate was collected in 1 ml-fractions and the fractions No. 4–7 were combined together and concentrated to dryness to yield 38.1 mg (45.4%) of the desired 1-N-[3-amino-2-hydroxypropionyl]-5,3′,4′-trideoxy-6′-N-methylkanamycin B in the form of its monocarbonate.

EXAMPLE 8

Synthesis of 1-N-[(S)-5-amino-2-hydroxyvaleryl]-5,3′,4′-trideoxy-6′-N-methylkanamycin B The same procedures as described in Example 7 were repeated but using 76 mg (0.204 mmole) of N-hydroxysuccinimide ester of (S)-5-p-methoxybenzyloxycarbonylamino-2-hydroxyvaleric acid in place of the 3-p-methoxybenzyloxycarbonylamino-2-hydroxypropionic acid N-hydroxysuccinimide ester to be reacted with the 3,2′,6′-tri-N-tert-butoxycarbonyl-3″-N-trifluoroacetyl-5,3′,4′-trideoxy-6′-N-methylkanamycin B.

After the elution of the Amberlite CG-50 column, the eluate fractions No. 11–18 were combined together and concentrated to dryness to give 47.2 mg (53.8%) of the title compound (monocarbonate).

What we claim is:

1. A compound of the formula (I)

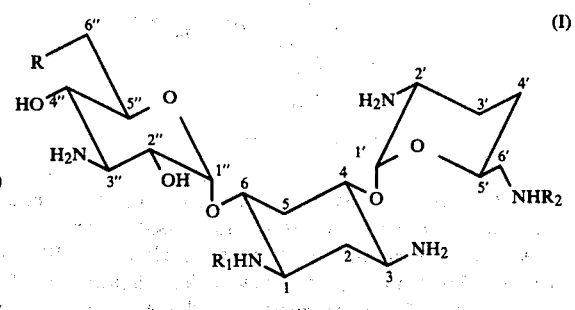

wherein R is a hydroxyl group or a hydrogen atom, $R_1$ is a hydrogen atom or an α-hydroxy-ω-aminoalkanoyl group of formula

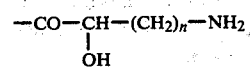

where n is an integer of 1, 2 or 3, and $R_2$ is a hydrogen atom or a methyl group, provided that $R_2$ is not a methyl group when R is a hydrogen atom, and provided that $R_2$ must be a methyl group when R is a hydroxyl group and $R_1$ is a hydrogen atom, and a pharmaceutically acceptable acid-addition salt of said compound.

2. The compound of claim 1 which is a 1-N-[α-hydroxy-ω-aminoalkanoyl]-5,3′,4′-trideoxykanamycin B or 1-N-[α-hydroxy-ω-aminoalkanoyl]-5,3′,4′,6″-tetradeoxykanamycin B represented by the formula (II)

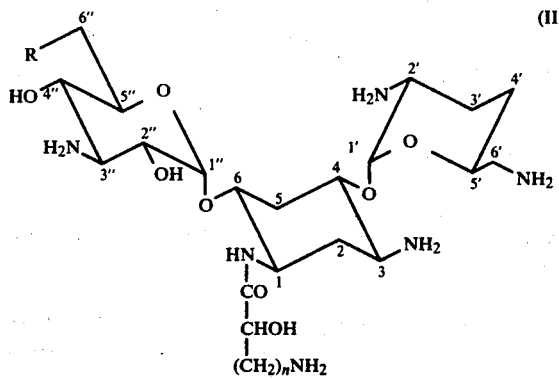

wherein R is a hydroxyl group or a hydrogen atom and n is an integer of 1, 2 or 3, and a pharmaceutically acceptable acid-addition salt of said compound.

3. The compound of claim 1 which is a 1-N-[α-hydroxy-ω-aminoalkanoyl]-5,3',4'-trideoxy-6'-N-methylkanamycin B represented by the formula (IV)

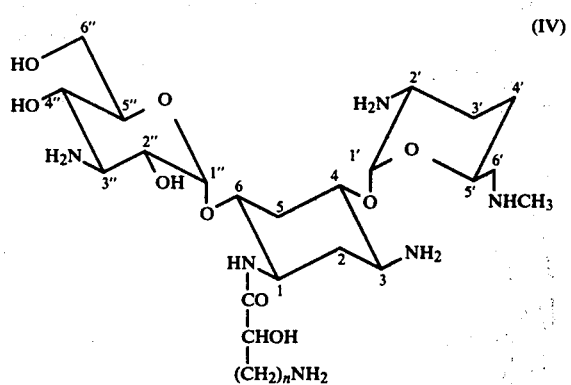

wherein n is an integer of 1, 2 or 3, and a pharmaceutically acceptable acid-addition salt of said compound.

4. The compound of claim 2 which is 1-N-[(S)-4-amino-2-hydroxybutyryl]-5,3',4'-trideoxykanamycin B; 1-N-[3-amino-2-hydroxypropionyl]-5,3',4'-trideoxykanamycin B; or 1-N-[(S)-4-amino-2-hydroxybutyryl]-5,3',4'6''-tetradeoxykanamycin B.

5. The compound of claim 3 which is 1-N-[3-amino-2-hydroxypropionyl]-5,3',4'-trideoxy-6'-N-methylkanamycin B; 1-N-[(S)-4-amino-2-hydroxybutyryl]-5,3',4'-trideoxy-6'-N-methylkanamycin B; or 1-N-[(S)-5-amino-2-hydroxyvaleryl]-5,3',4'-trideoxy-6'-N-methylkanamycin B.

6. The compound of claim 1 which is 5,3',4',6''-tetradeoxykanamycin B represented by the formula (III)

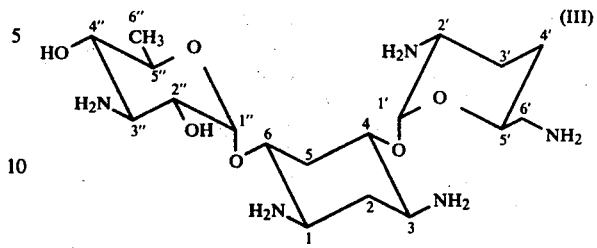

and a pharmaceutically acceptable acid-addition salt of said compound.

7. The compound of claim 1 which is 5,3',4'-trideoxy-6'-N-methylkanamycin B represented by the formula (V)

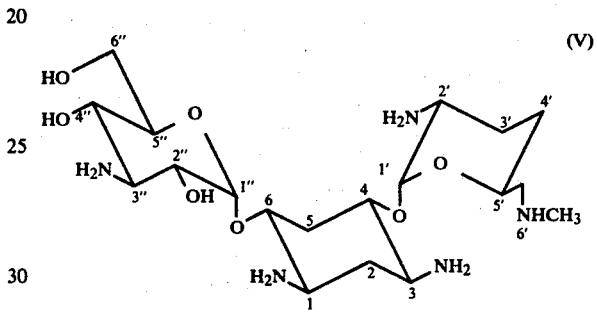

and a pharmaceutically acceptable acid-addition salt of said compound.

8. An antibacterial composition comprising as the active ingredient a 1-N-[(α-hydroxy-ω-aminoalkanoyl)-5,3',4'-trideoxykanamycin B or a pharmaceutically acceptable acid-addition salt, a 1-N-(α-hydroxy-ω-aminoalkanoyl-5,3',4',6''-tetradeoxykanamycin B or a pharmaceutically acceptable acid-addition salt or 5,3',4',6''-tetradeoxykanamycin B or a pharmaceutically acceptable acid-addition salt in an anti-bacterially effective amount to inhibit the growth of bacteria, in combination with a carrier for the active ingredient compound.

9. An antibacterial composition comprising as the active ingredient a 1-N-[α-hydroxy-ω-aminoalkanoyl-5,3',4'-trideoxy-6'-N-methylkanamycin B or 5,3',4'-trideoxy-6'-N-methylkanamycin B or a pharmaceutically acceptable acid-addition salt thereof as defined in claim 3 or 7 in an antibacterially effective amount to inhibit the growth of bacteria, in combination with a carrier for the active ingredient compound.

* * * * *